United States Patent
Roh et al.

(10) Patent No.: US 11,464,573 B1
(45) Date of Patent: Oct. 11, 2022

(54) METHODS AND SYSTEMS FOR REAL-TIME ROBOTIC SURGICAL ASSISTANCE IN AN OPERATING ROOM

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/731,008

(22) Filed: Apr. 27, 2022

(51) Int. Cl.
| | |
|---|---|
| *A61B 34/10* | (2016.01) |
| *A61B 5/022* | (2006.01) |
| *A61B 5/00* | (2006.01) |
| *A61B 34/00* | (2016.01) |
| *G16H 50/20* | (2018.01) |
| *G16H 20/40* | (2018.01) |

(52) U.S. Cl.
CPC .......... *A61B 34/10* (2016.02); *A61B 5/02233* (2013.01); *A61B 5/746* (2013.01); *A61B 34/25* (2016.02); *G16H 20/40* (2018.01); *G16H 50/20* (2018.01); *A61B 2034/107* (2016.02); *A61B 2034/108* (2016.02); *A61B 2034/252* (2016.02); *A61B 2034/254* (2016.02); *A61B 2034/256* (2016.02)

(58) Field of Classification Search
None
See application file for complete search history.

(56) References Cited

U.S. PATENT DOCUMENTS

| | | | | |
|---|---|---|---|---|
| 6,058,323 | A * | 5/2000 | Lemelson | A61B 17/320758 600/408 |
| 6,718,196 | B1 * | 4/2004 | Mah | A61B 8/4218 600/117 |
| 7,338,526 | B2 * | 3/2008 | Steinberg | A61B 34/70 623/17.11 |
| 8,572,290 | B1 * | 10/2013 | Mukhopadhyay | G06N 20/00 709/251 |
| 10,105,149 | B2 * | 10/2018 | Haider | A61B 34/20 |
| 10,467,509 | B2 * | 11/2019 | Albadawi | G06F 21/32 |
| 10,517,681 | B2 * | 12/2019 | Roh | G06N 3/08 |
| 10,729,502 | B1 * | 8/2020 | Wolf | G16H 20/40 |

(Continued)

*Primary Examiner* — Carl H Layno
*Assistant Examiner* — Manolis Pahakis
(74) *Attorney, Agent, or Firm* — Perkins Coie LLP

(57) ABSTRACT

Methods, apparatuses, and systems for providing real-time surgical assistance to a surgical robot using an imaging module, a context computer module, and a quantum analysis module are disclosed. The imaging module receives one or more data related to a patient from an intra-operative database and performs a first step analysis based on the received data. The context computer module determines a type of resource required for analysis based on data received from a historical database and the intra-operative database. The quantum analysis module receives data from the imaging module and the context computer module. The quantum analysis module receives real-time data from operation room (OR) equipment and performs quantum analysis on the received data and real-time data. The quantum analysis module facilitates real-time surgical assistance and recommendations to the surgical robot.

20 Claims, 17 Drawing Sheets

(56) References Cited

U.S. PATENT DOCUMENTS

| | | | | |
|---|---|---|---|---|
| 10,874,464 B2* | 12/2020 | Roh | | G16H 50/20 |
| 11,191,181 B1* | 11/2021 | Tandon | | B25J 9/1679 |
| 11,195,616 B1* | 12/2021 | Seemakurty | | A61B 5/318 |
| 11,304,760 B1* | 4/2022 | Roh | | A61B 34/10 |
| 11,304,761 B2* | 4/2022 | Roh | | G16H 40/63 |
| 11,350,994 B2* | 6/2022 | Roh | | G16H 50/70 |
| 11,389,102 B2* | 7/2022 | Haeusser | | A61B 5/0044 |
| 11,389,248 B1* | 7/2022 | Roh | | A61B 34/10 |
| 2007/0016006 A1* | 1/2007 | Shachar | | A61B 5/062 |
| | | | | 600/407 |
| 2008/0275349 A1* | 11/2008 | Halperin | | A61B 5/447 |
| | | | | 600/364 |
| 2011/0093416 A1* | 4/2011 | Pelossof | | G06N 20/00 |
| | | | | 706/12 |
| 2014/0046128 A1* | 2/2014 | Lee | | A61B 34/30 |
| | | | | 600/102 |
| 2014/0200575 A1* | 7/2014 | Spector | | A61B 18/14 |
| | | | | 606/40 |
| 2018/0182475 A1* | 6/2018 | Cossler | | G16H 50/50 |
| 2018/0296281 A1* | 10/2018 | Yeung | | G06T 7/13 |
| 2018/0360543 A1* | 12/2018 | Roh | | G16H 20/40 |
| 2019/0069957 A1* | 3/2019 | Barral | | G06N 20/10 |
| 2019/0163530 A1* | 5/2019 | Tien | | G06F 9/5072 |
| 2019/0189259 A1* | 6/2019 | Clark | | G16H 10/60 |
| 2019/0262084 A1* | 8/2019 | Roh | | G16H 40/60 |
| 2019/0380791 A1* | 12/2019 | Fuerst | | B25J 13/087 |
| 2020/0138319 A1* | 5/2020 | Spector | | A61B 5/287 |
| 2020/0184027 A1* | 6/2020 | Dolan | | G01S 13/931 |
| 2020/0237452 A1* | 7/2020 | Wolf | | G06F 3/048 |
| 2020/0245885 A1* | 8/2020 | Haeusser | | A61B 5/0044 |
| 2020/0273575 A1* | 8/2020 | Wolf | | G06V 20/40 |
| 2020/0273581 A1* | 8/2020 | Wolf | | A61B 1/000094 |
| 2020/0345261 A1* | 11/2020 | Haeusser | | A61B 5/361 |
| 2020/0376183 A1* | 12/2020 | El Katerji | | A61M 60/50 |
| 2020/0405148 A1* | 12/2020 | Tran | | G16H 50/20 |
| 2021/0076966 A1* | 3/2021 | Grantcharov | | G06N 20/00 |
| 2021/0166812 A1* | 6/2021 | Amir | | A61B 5/0053 |
| 2021/0196108 A1* | 7/2021 | Shelton, IV | | G01B 11/25 |
| 2021/0199557 A1* | 7/2021 | Shelton, IV | | A61B 18/12 |
| 2021/0244374 A1* | 8/2021 | Zhao | | A61B 6/482 |
| 2021/0259765 A1* | 8/2021 | Narayan | | A61B 18/1492 |
| 2021/0350897 A1* | 11/2021 | Shelton, IV | | A61M 5/172 |
| 2021/0369394 A1* | 12/2021 | Braido | | A61B 5/745 |
| 2021/0378579 A1* | 12/2021 | Doron | | A61B 5/287 |
| 2022/0114014 A1* | 4/2022 | Chen | | G06K 9/6272 |
| 2022/0117682 A1* | 4/2022 | Malackowski | | A61B 90/361 |

* cited by examiner

612

INTRA-OPERATIVE DATABASE

PATIENT DATA

| NAME | AGE | WEIGHT | DIAGNOSIS | IMAGES | FAMILY MEDICAL HISTORY |
|------|-----|--------|-----------|--------|------------------------|
| Alex | 34 | 74 | Leg Fracture | Image 1 | • High Blood Pressure to Mother |
|      |     |        |              | Image 2 | • Diabetes to Father |
|      |     |        |              | Image 3 | • Grandfather Father Died of Kidney Cancer |

OPERATIONAL DATA

| NAME | REAL-TIME IMAGING DATA | PRE-PLAN FOR OPERATION | TYPE OF OPERATION | SURGICAL SITE | EXPECTED OUTCOME |
|------|------------------------|------------------------|-------------------|---------------|------------------|
| Alex | Image of Left Leg | Medication for Numbing the Left Leg | Surgical Operation for Fracture | Lower Portion of Left Leg | Stable Left Leg with No Pain and No Side Effects (Including Normal Blood Pressure) |
|      | MRI Scan |  |  |  |  |
|      | Image of Right Leg |  |  |  |  |

PERSONNEL MANIFEST

| NAME | DESIGNATION | EXPERIENCE | HEALTH CONDITION |
|------|-------------|------------|------------------|
| Maria | Scrub Tech | 2 Years | Normal |
| Peter | Nurse | 1 Year | Normal |
| Troy | Circulating Tech | 3 Years | Normal |

*FIG. 7*

HISTORICAL DATABASE

| NAME | LENGTH OF OPERATION | EQUIPMENT USED | SURGICAL WORKFLOW | FOLLOW-UP WITH SURGEON | PATIENT SURVEY DATA |
|---|---|---|---|---|---|
| Alex | 4 Hours | X-Ray, MRI, Surgical tools | | On time | Satisfied |
| Frank | 6 Hours | X-Ray, MRI, Surgical tools | | On time | Unhappy |
| Marc | 6 Hours | X-Ray, MRI, Surgical tools | | Missed couple of times | Satisfied |
| Alice | 5 Hours | X-Ray, MRI, Surgical tools | | On time | Satisfied |

CONTEXT COMPUTER DATABASE

| TYPE OF COMPUTER (RESOURCE) | COST OF RESOURCE | COMPUTATIONAL CAPABILITY | AVAILABILITY |
|---|---|---|---|
| Classical computer | $ 100 | 1 GHz | 10 |
| Super computer | $ 300 | 3 GHz | 7 |
| Quantum computer | $ 500 | 5 GHz | 3 |

*FIG. 11*

METHODS AND SYSTEMS FOR REAL-TIME ROBOTIC SURGICAL ASSISTANCE IN AN OPERATING ROOM

TECHNICAL FIELD

The present disclosure is generally related to automated and robotic surgical procedures and specifically to methods and systems for real-time robotic surgical assistance in an operating room.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 illustrates a structure of an example intra-operative database for real-time robotic surgical assistance in an operating room, in accordance with one or more embodiments.

FIG. 8 illustrates a structure of an example historical database for real-time robotic surgical assistance in an operating room, in accordance with one or more embodiments.

FIG. 11 illustrates a structure of an example context computer database for real-time robotic surgical assistance in an operating room, in accordance with one or more embodiments.

DETAILED DESCRIPTION

Figure 1:
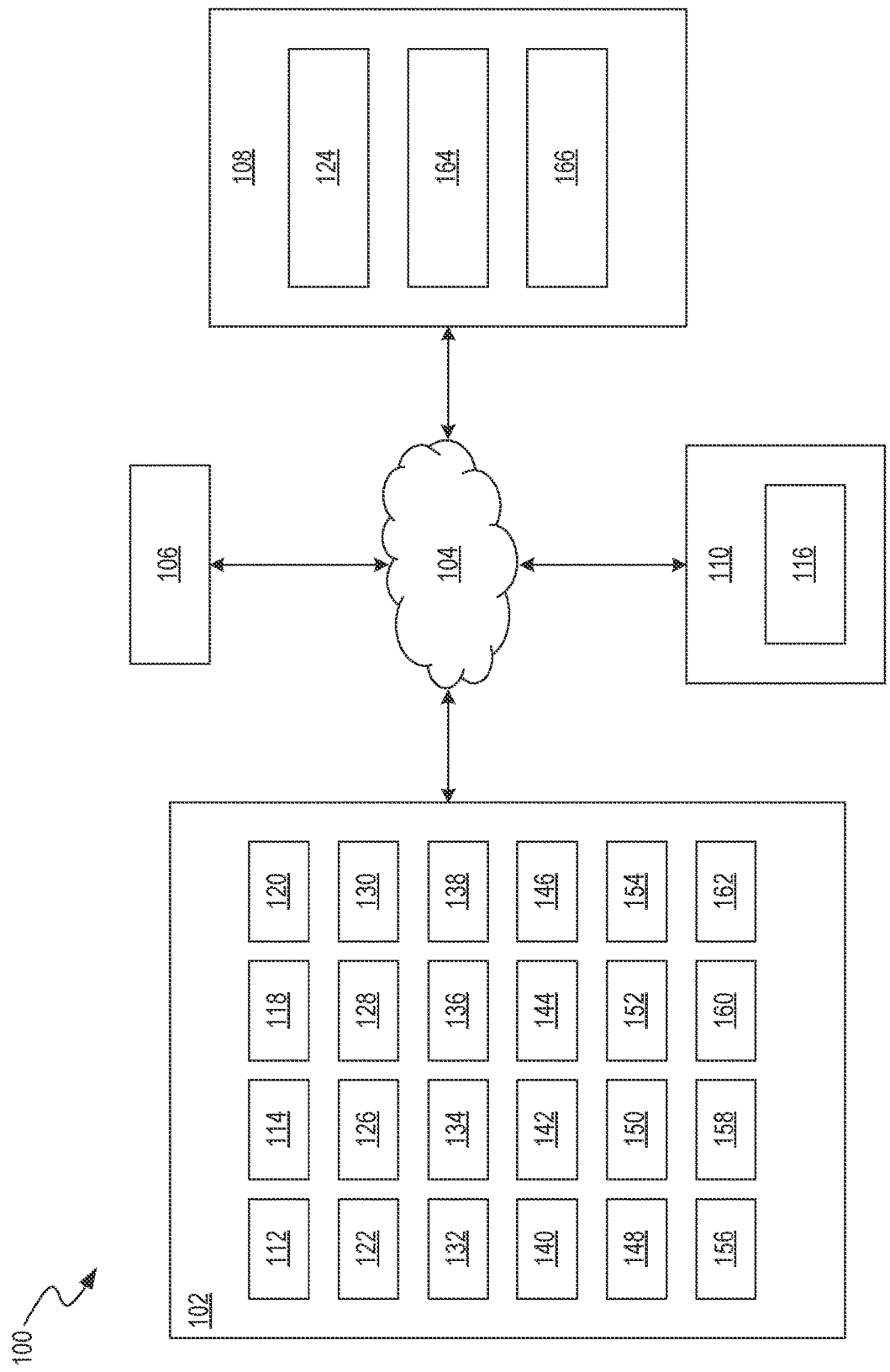
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610a") described as a single instance. Further, plural instances (e.g., "610") refer collectively to a set of components, operations, or structures (e.g., "610a") described as a single instance. The description of a single component (e.g., "610a") applies equally to a like-numbered component (e.g., "610b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

Surgical procedures can involve measurements and observations that are made during a surgery in an Operating Room (OR), using OR equipment. Further, such measurements and observations typically require an expert opinion, such as from a pathologist, radiologist, etc., utilizing medical imaging techniques, patient monitoring devices, etc., before performing any surgery. The opinion of the expert is important as it relies on a detailed analysis and provides a recommendation related to the surgery. However, the process of acquiring an opinion from an expert can consume much time. First, measurements and observations made in the OR equipment are taken to the expert for their opinion or analysis. Second, the experts consume time to analyze the observations. Finally, the expert's opinion reports are taken back to the OR for resuming the surgery.

The embodiments disclosed herein describe methods, apparatuses, and systems for real-time robotic surgical assistance in an operating room. In some embodiments, the time and effort to procure an expert opinion is reduced using a computer assisted surgery (CAS) system. CAS includes pre-operative planning of a surgical procedure, and presenting pre-operative diagnostic information, images, and status information about the surgical procedure. CAS can be used in operating rooms, outpatient clinics, and interventional radiology suites. CAS is sometimes referred to as robotic surgery. CAS devices enable a surgical robot or surgeon to use computer and software technology to control and move surgical instruments through one or more tiny incisions in the patient's body (minimally invasive surgery) for a variety of surgical procedures.

In some embodiments, methods, apparatuses, and systems for providing real-time surgical assistance to a surgical robot use an imaging module, a context computer module, and a quantum analysis module. The imaging module receives data related to a patient from an intra-operative database and performs a first step analysis based on the received data. For example, the data can include stored reference patient images, stored reference procedure data, or the like. The stored reference procedure data describes previous surgical procedures associated with the patient and the surgical procedure. The context computer module determines a type of resource required for analysis based on data received from a historical database and the intra-operative database. The quantum analysis module receives data from the imaging module and the context computer module. The quantum analysis module receives real-time data from operation room (OR) equipment and performs quantum analysis on the received data and real-time data. The quantum analysis module facilitates real-time surgical assistance and recommendations to the surgical robot.

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgical system disclosed uses computer networks, the Internet, intranets, and supporting technologies to implement a cost-effective technology to collect, transmit, store, analyze, and use surgical information in electronic formats. As a result, surgical robots can use the embodiments to collect and analyze vast amounts of information, resulting in early diagnoses. The disclosed methods reduce the amount of noise, and increase the resolution, replicability, efficiency, and accuracy in collecting and analyzing information. Further, the embodiments disclosed herein enable meta-analyses for more-elaborate diagnostic procedures and reduce the need for repetitive invasive diagnostic testing. In addition, the disclosed systems enable continuous monitoring and analysis of the health of the patient in order to provide real-time assistance to a surgical robot or surgeon during a surgery procedure.

The robotic surgery technologies disclosed further offer valuable enhancements to medical or surgical processes through improved precision, stability, and dexterity. The disclosed methods make medical procedures safer and less costly for patients. The embodiments disclosed enable more accurate surgery to be performed in more minute locations on or within the human body. The embodiments also address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate.

Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"— of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker (e.g., the speaker 632 of FIG. 6), etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
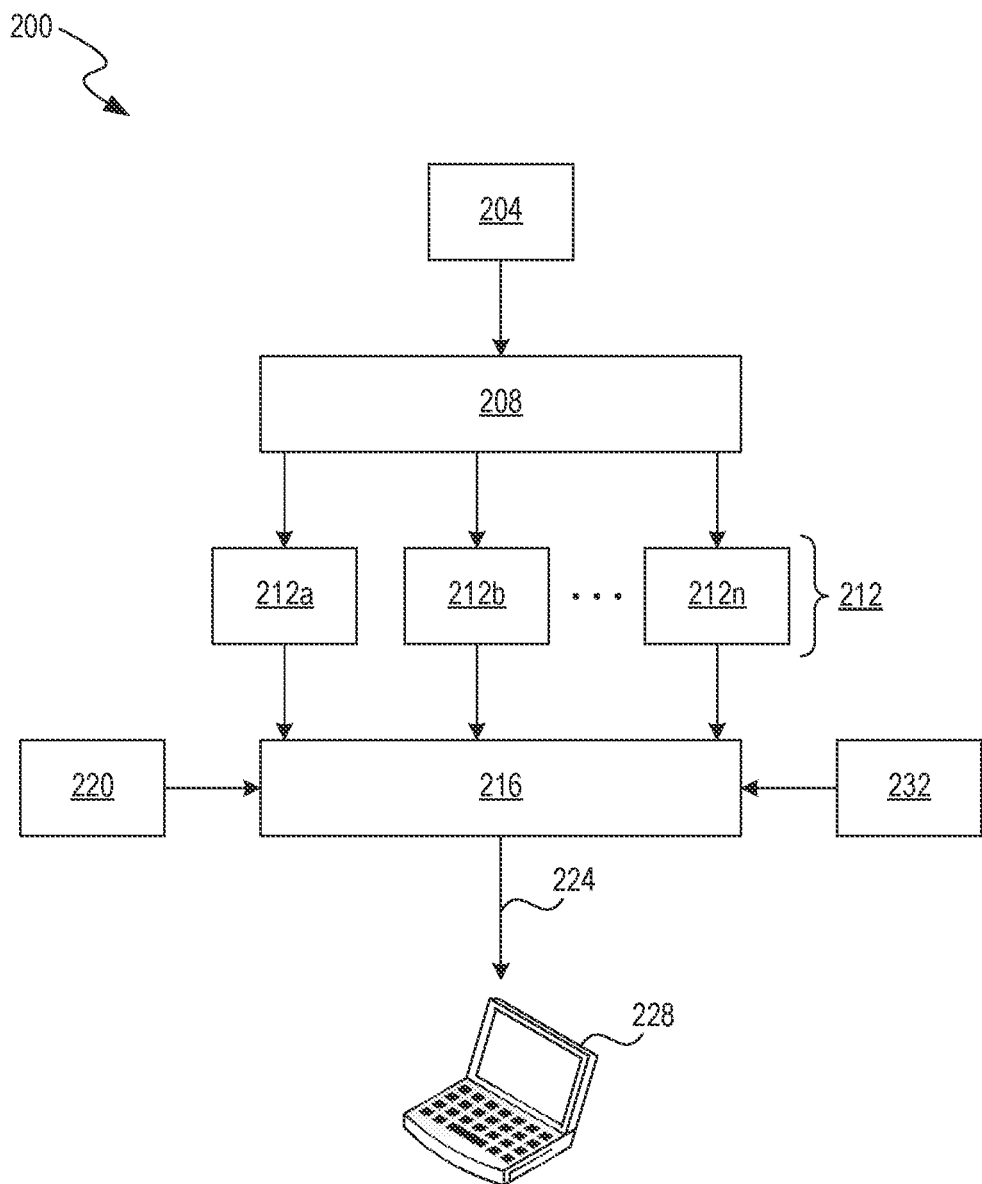
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . 212n. The feature extraction module 208 reduces the redundancy in the input data 204, e.g., repetitive data values, to transform the input data 204 into the reduced set of features 212, e.g., features 212a, 212b, . . . 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker (e.g., the speaker 632 of FIG. 6), etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
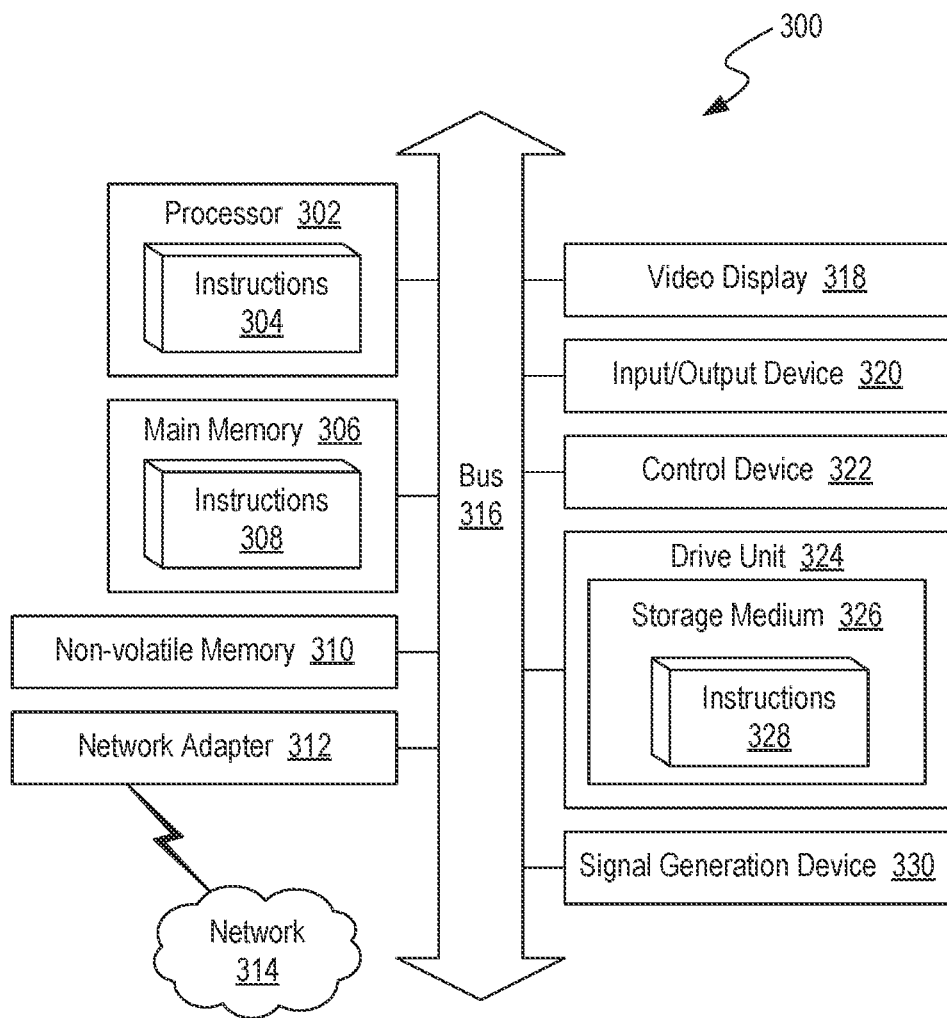
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
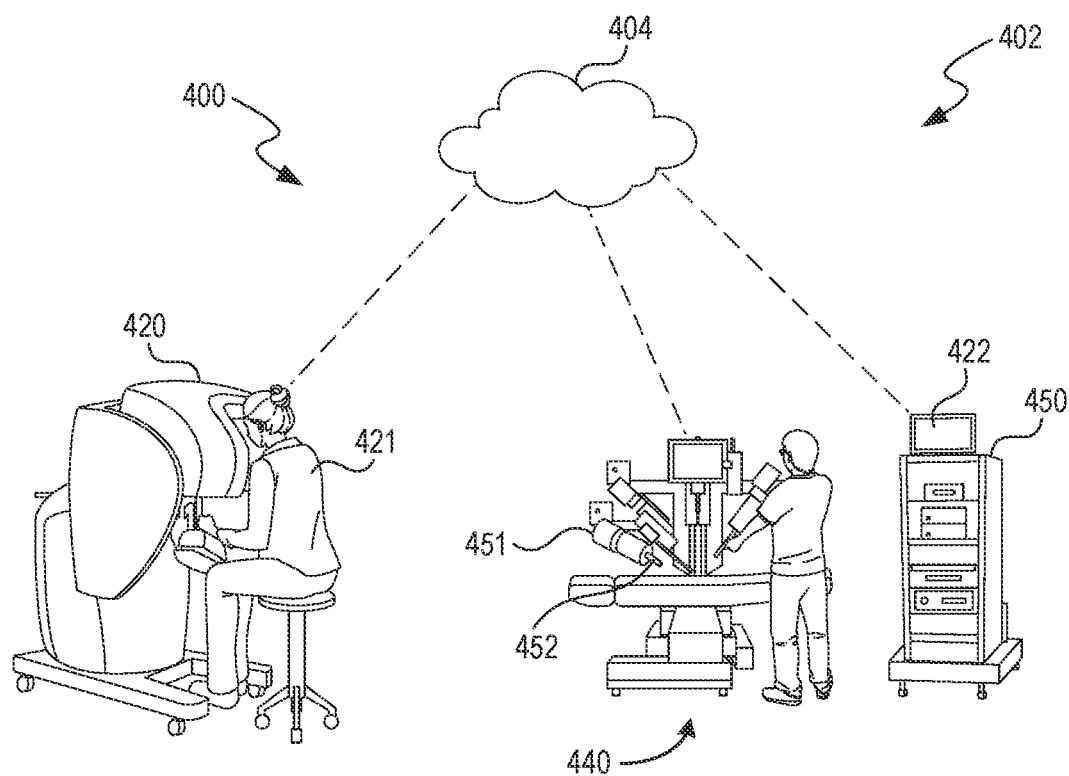
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5.

For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
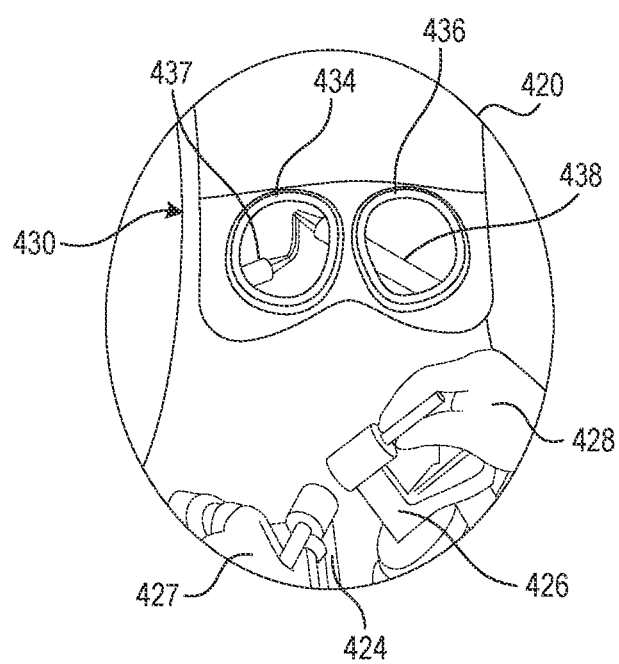
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be preprogrammed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
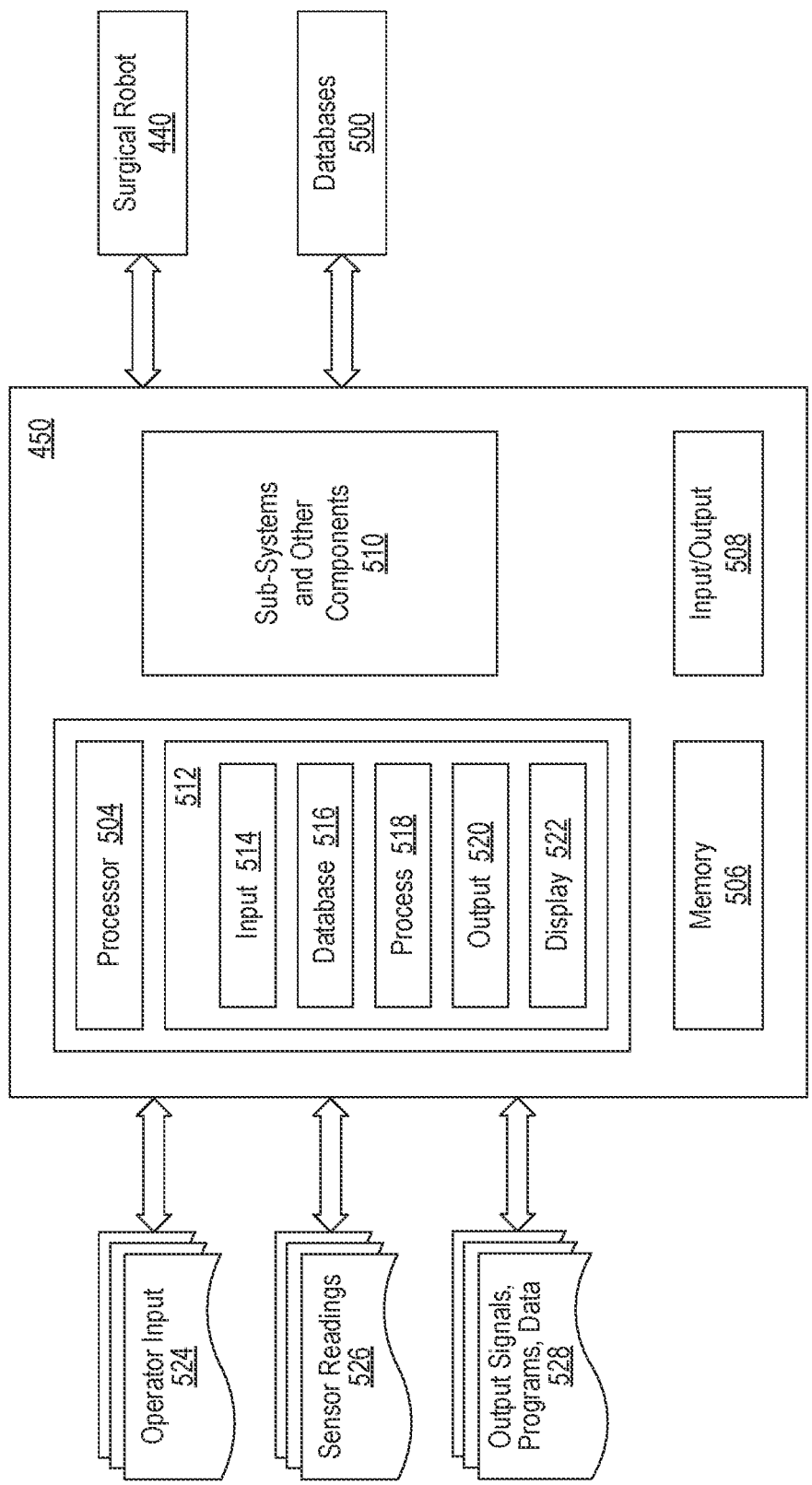
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
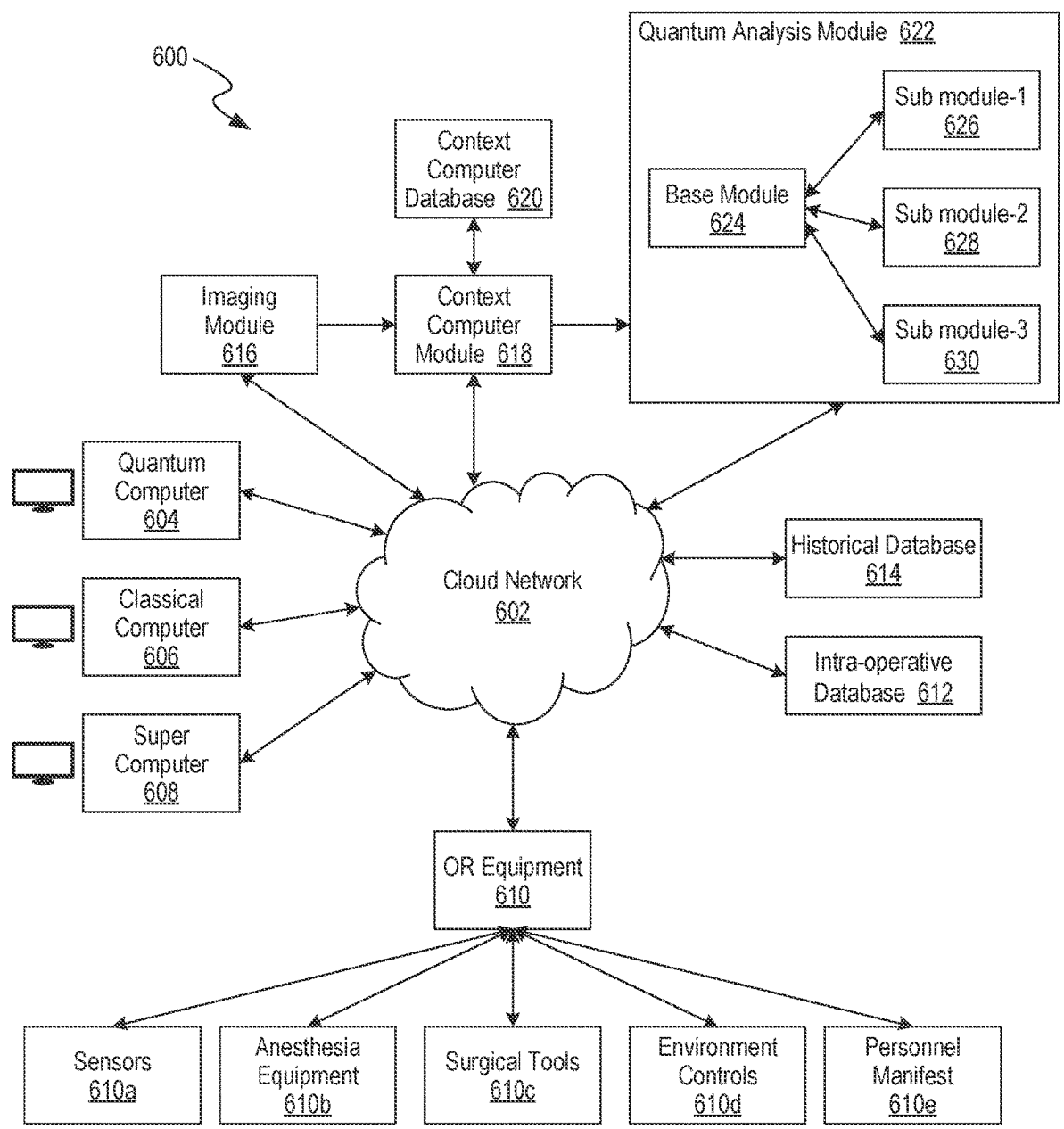
FIG. 6 is a block diagram illustrating an example robotic surgical system for real-time robotic surgical assistance in an operating room, in accordance with one or more embodiments.

FIG. 6 is a block diagram illustrating an example robotic surgical system 600 for real-time robotic surgical assistance in an operating room, in accordance with one or more embodiments. An example operating room 102 is illustrated and described in more detail with reference to FIG. 1. The robotic surgical system 600 can include a cloud network 602, a quantum computer 604, a classical computer 606, and a supercomputer 608. A robotic "action" refers to one or more physical movements of a surgical robot (e.g., the surgical robot 440), such as aligning a surgical implant component or a surgical tool 154 (see FIG. 1), initiating the rotation of a rotary surgical tool, applying an axial force to a surgical tool 154, etc. The robotic surgical system 600 is implemented using the components of the example computer system 300 illustrated and described in more detail with reference to FIG. 3. Likewise, embodiments of the robotic surgical system 600 can include different and/or additional components or can be connected in different ways.

In some embodiments, the quantum computer 604, the classical computer 606, and the supercomputer 608 are connected to the cloud network 602, for performing analysis on information related to the system 600. Further, the system 600 can include an Operation Room (OR) equipment 610. The OR equipment 610 can further include at least one sensor 610a, an anesthesia equipment 610b, at least one surgical tool 610c, at least one environment control equipment 610d, and a personnel manifest 610e, for receiving information from the OR. In embodiments, the at least one sensor 610a, the anesthesia equipment 610b, the at least one surgical tool 610c, the at least one environment control equipment 610d, and the personnel manifest 610e may be connected to the cloud network 602, via the OR equipment 610.

The system 600 can further include an intra-operative database 612 and a historical database 614 for storing information associated with the system 600. In some embodiments, the system 600 performs a computer-implemented method for providing real-time surgical assistance to a surgical robot. For example, the system 600 includes an imaging module 616 for monitoring image data from the OR, and a context computer module 618, for performing analysis related to the system 600 for real-time assistance in the OR. Further, the context computer module 618 can operate in conjunction with a context computer database 620, for storing information related to the context computer module 618. Further, the context computer module 618 can be coupled to a quantum analysis module 622 for finding patterns and correlations in information received from the context computer module 618. In some embodiments, the quantum analysis module 622 operates on the quantum computer 604.

The cloud network 602 can be implemented using a collection of server devices to provide one or more services to coupled devices. Further, the cloud network 602 can be coupled to the quantum computer 604, the classical computer 606, or the supercomputer 608. Further, the cloud network 602 can be a wired and/or a wireless network. The cloud network 602, if wireless, can be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques, known in the art. The communication network can allow ubiquitous access to shared pools of configurable resources and higher-level services that can be rapidly provisioned with minimal management effort, often over the Internet. The communication network can rely on sharing of resources to achieve coherence and economies of scale, such as a public utility, while third-party clouds enable organizations to focus on their core businesses instead of expending resources on computer infrastructure and maintenance. Additionally, the cloud network 602 can be communicatively coupled to the OR equipment 610, the imaging module 616, the context computer module 618, and the quantum analysis module 622, for real-time assistance in the OR. The cloud network 602 may also be synchronized with the intra-operative database 612 and the historical database 614 to store real-time as well as historical information associated with the surgical procedure in the OR. For example, the historical information can include stored reference patient images and/or stored reference procedure data. The stored reference procedure data describes previous surgical procedures associated with the patient (e.g., previous surgical procedures performed on similar or matching patients, previous surgical procedures performed on the same patient, etc.), the surgical procedure (e.g., similar or matching surgical procedures, surgical steps, etc.), or the like.

In some embodiments, the quantum computer 604 is a machine that performs quantum computations. Further, quantum computing can be the exploitation of collective properties of quantum states, such as superposition and entanglement, to perform computation. The quantum computer 604 can use the properties of quantum physics to store data and perform computations to enable diagnostic assistance, precision medicine and pricing that are central to the healthcare industry's ongoing transformation. In one exemplary embodiment, the quantum computer 604 can be obtained from a manufacturer such as, but not limited to, IBM or Microsoft. In embodiments, the quantum computer 604 is able to solve certain computational problems, such as integer factorization, substantially faster than classical computers. Further, the quantum computer 604 calculates in qubits, which can represent 0 and 1 at the same time. The power consumed by the quantum computer 604 can increase as the number of qubits increases. Further, the quantum computer 104 sometimes needs cooling. The use of the quantum computer 604 facilitates solving optimization problems, data analysis, and simulations. Further, the quantum computer 604 is connected to the cloud network 602.

In embodiments, the classical computer 606 is present in the OR. In another embodiment, the classical computer 606 is connected to the cloud network 602. The classical computer 606 can operate using binary logic and carries out logical operations using definite positions of physical states. In some embodiments, each element of the classical computer 606 is implemented in binary code (1s and 0s); the digital states are translated into voltage levels in transistors: high voltage is represented by 1, and low voltage by 0. Further, the classical computer 606 can make use of programming computer language constructs, such as "AND" and "NOT." Further, the classical computer 606 increases power consumption in a 1:1 relationship with the number of transistors. The classical computer 606 has a very low error rate and can operate at room temperature.

In embodiments, the supercomputer 608 is present in the OR. Further, the supercomputer 608 can be connected to the cloud network 602. The supercomputer 608 provides a very high level of performance as compared to a general-purpose computer and can be used for a wide range of computationally intensive tasks in various fields, including quantum mechanics, weather forecasting, climate research, etc.

In some embodiments, the system 600 captures real-time images, during a surgical procedure, of one or more surgical sites in a body of a patient undergoing the surgical procedure. For example, the real-time images can include high-resolution video, X-rays, digital still images, etc. The capturing is performed using one or more imaging devices. For example, the OR equipment 610 includes the sensors 610a, which can include imaging devices such as, but not limited to, magnetic resonance imaging (MRI), X-radiation (X-Ray), and other imaging devices. Such imaging devices can use strong magnetic fields and radio waves to produce detailed images of the inside of a patient's body or use radiations to create pictures inside of the patient's body. In some embodiments, the system 600 generates real-time sensor data using the one or more sensors 610a in the operating room. The real-time sensor data indicates one or more physiological parameters of the patient undergoing the surgical procedure. For example, the sensors 610a can also include patient monitoring devices such as, but not limited to, electroencephalogram (EEG) (which detects abnormalities in brain waves or in the electrical activity of a patient's brain), electrocardiography (ECG), oxygen saturation from a pulse oximeter (SpO2), blood pressure, or other patient monitoring devices.

In embodiments, the anesthesia equipment 610b includes sedation devices or pharmaceuticals. The anesthesia equipment 610b is a continuous-flow anesthetic machine, which provides a steady flow of air containing a regulated supply of gas to deliver general anesthesia to patients as they undergo a medical procedure. The anesthesia equipment 610b can include an oxygen mask or an anesthetic vaporizer. Further, the anesthesia equipment 610b can differ in appearance, size, and degree of sophistication. The anesthesia equipment 610b can include sections for: ventilation, peripheral nerve stimulator, space for monitoring equipment, accessories, storage space, or a worktop.

In embodiments, the system 600 includes the surgical tools 610c, which can include a surgical robot (see FIGS. 4A-4B) and handheld tools (see FIG. 1). Further, the surgical tools 610c can be connected to the cloud network 602. The surgical tools are used for carrying out desired effects or performing specific actions during a surgery or operation, such as modifying biological tissue, or to provide access for viewing it. The surgical robot can further include arms, end-effectors, and software. In embodiments, the software can include autonomous and manual controls. Further, the handheld surgical tools may include forceps, retractors, dilators, or graspers. Such surgical tools 610c can facilitate a surgical robot in the OR to perform various surgical procedures.

Further, the environment controls 610d can include at least lighting, heating, ventilation, or air conditioning (HVAC) to control the temperature of the environment. The environment controls 610d can control audio noise associated with the OR. A goal is to provide thermal comfort and acceptable indoor air quality for surgery. HVAC can be defined as a sub-discipline of mechanical engineering, based on the principles of thermodynamics, fluid mechanics and heat transfer. Further, refrigeration is sometimes added to the field's abbreviation, as HVAC&R, HVACR, or HACR.

Further, HVAC is an important part of residential structures such as single-family homes, apartment buildings, hotels, senior living facilities, medium to large industrial buildings, and office buildings such as skyscrapers and hospitals. HVAC can be used in vehicles such as cars, trains, airplanes, ships and submarines, and in marine environments where safe and healthy building conditions are regulated with respect to temperature and humidity, using fresh air from outdoors.

Further, the personnel manifest 610e can include information related to any or all of the attending staff in the operating room. In embodiments, the personnel manifest 610e includes information related to, but not limited to, surgeons, anesthesiologists, surgical scrub technicians, circulating surgical technicians, etc. Further, the personnel manifest 610e may correspond to name, age, experience, and health conditions of the attending staff in the operating room. For example, "data for 'Maria' who is a scrub technician, having an experience of 2 years, and whose medical condition is normal, is present in the operating room."

In some embodiments, the system 600 provides voice control functionality for surgical tools 154 (see FIG. 1). A surgical robot is a robotic system designed to perform surgery and, in some cases, assist a surgeon in performing a surgical operation on a patient. The surgical robot includes at least one controller and at least one robotic arm having at least one end effector or at least one imaging device. The surgical robot can further include a user interface for accepting control inputs from a user, such as a surgeon or other medical professional and a communications interface for transmitting and receiving data to and from the cloud for the purpose of training an artificial intelligence (see FIG. 2) operating within the surgical robot or receiving commands from a remote user or an artificial intelligence existing external to the surgical robot. The robotic arm is a mechanically actuated arm or lever with at least two degrees of freedom. The robotic arm will typically include the end effector or the imaging device and can include both the end effector and the imaging device. The robotic arm can additionally be capable of changing the end effector to facilitate multiple functions and operation of a variety of tools. The robotic arm can be manually controlled or operated in an autonomous or semi-autonomous mode. The surgical robot can have one robotic arm or multiple robotic arms, each of which can be operated independently by one or more users or autonomous systems or a combination of users and autonomous systems.

The system 600 can store user profiles that include, without limitation, speech recognition profiles, reference speech input, speech characteristics, user-specific surgical techniques, user preferences, etc. The speech characteristics can include, without limitation, volume, pace, resonance, intonation, pitch, or the like. Acoustic models, language models, pronunciation dictionaries, feature extractors, feature vectors, decoders, word output generators, or the like can be used to recognize speech based on acoustic models, language models, etc.

In some embodiments, a natural language processing model performs natural language processing that includes, without limitation, named entity recognition (e.g., identifying words, phrases, etc.), co-reference resolution, sentiment analysis, tagging (e.g., speech tagging, grammatical tagging, etc.), speech recognition, natural language generation, and/or natural language processing steps. The named entity recognition identifies prompts or phrases commonly used by the surgeon. The system can perform named entity recognition based on captured data (e.g., images captured by cameras) to increase accuracy. For example, the named entity recognition can identify a "tool" of speech input as the tool visible to the surgeon via the monitor console. The system can perform co-reference resolution steps to identify multiple words, such as "tool," "end effector," "instrument," etc., as referring to the same device. Sentiment analysis is used to extract subjective qualities, such as excitement, calmness, or other subjective qualities that may indicate the status of the surgical procedure. Tagging is performed to determine a particular word or string of text based on its use in context. For example, tagging can be used to identify verbs, nouns, etc. For example, if a surgeon states "move the scalpel two inches," tagging can be used to identify the scalpel as a noun and "move" as the verb.

Speech recognition is used for speech-to-text processing to convert speech input into text data. The text data is analyzed using text data processing techniques. In some embodiments, natural language processing includes word sense disambiguation to determine the meaning of a word or phrase having multiple meanings through a process of, for example, semantic analysis. The surgical plan, anatomical data, and other information can be used in combination with speech processing techniques to perform word sense disambiguation. The cloud discussed herein can store databases for surgical techniques to perform word sense disambiguation comparisons.

In some embodiments, the system can identify a user associated with the speech input and can determine whether the user is authorized to control the robotic system. In response to determining that the user is authorized, the system can generate one or more actions to be performed by the robot as discussed below. The modules in the cloud can analyze user profiles for each of the surgical team members to perform user identification, authorization, etc. The modules in the cloud can be trained using pre-operative and intraoperative speech training based on the surgical plan, obtained anatomical data, or the like.

The modules in the cloud can be used in telesurgery applications by, for example, receiving speech input from a physician at a remote location. A remote physician can provide speech input via a telephone connected to a computer, network device, smartphone, tablet, or other speech input device. This allows a physician to control at least a portion of telesurgery procedures using speech input while viewing the procedure on a remote computing device. Advantageously, physicians can control surgical procedures without having access to joysticks or other robotic-specific inputs. In some procedures, a physician at the operating room can control a portion of a surgical procedure and a remote physician can control another portion of the surgical procedure. This allows coordination between local surgical robots and remote physicians. In some procedures, a surgery module can receive input from a local surgical robot and a remote physician and determine which input controls the instruments of the robotic surgery system. To increase accuracy, the modules in the cloud can use a user-specific speech processing module for each physician. The user-specific speech processing module can be trained pre-operatively using speech input from each physician.

An end effector is the end of the robotic arm that performs actions. The end effector is typically a tool or device for interacting with a physical object and can be a surgical tool intended for acting upon or within a patient or can be a gripping device for securing a separate surgical tool to the robotic arm. The end effector can be permanently affixed to the end of the robotic arm or can be detachable allowing for a system of interchangeable end effectors which can alternatively be selected and swapped by a single robotic arm or multiple robotic arms. The end effector can include features such as lights or other illumination devices, surgical tools, imaging devices, etc. The controller is a logic device or processor for preforming a series of logic operations. Traditionally, the controller is comprised of transistors arranged on a silicon substrate, although the controller can be comprised of any materials and substrates which form a logic circuit. Common logic circuit elements include OR gates, AND gates, XOR gates, NOR gates, NAND gates, etc. The controller can be a microcontroller or a central processing unit (CPU) in a computer. Similarly, a graphical processing unit (GPU) can be used as a controller. The controller can additionally be comprised by the logic element of a quantum computer. The controller uses logic operations to perform computations and can be in communication with the memory, for storing data, and a communications interface, for sending and receiving data to and from other controllers or devices.

FIG. 7 illustrates a structure of an example intra-operative database 612 for real-time robotic surgical assistance in an operating room, in accordance with one or more embodiments. An example operating room 102 is illustrated and described in more detail with reference to FIG. 1. As discussed herein, the system 600 can include one or more databases. A database stores a systematic collection of data used for electronic storage and manipulation of data. In embodiments, the database may be of various types such as, but not limited to, a centralized database, cloud database, or a network database. The one or more databases may include the intra-operative database 612 and the historical database 614 (see FIG. 7-8). The intra-operative database 612 can include one or more data received from the sensors 610a, one or more details of the patient such as, but not limited to, name, age, weight, diagnosis, patient images, and medical history of the patient and their family. The intra-operative database 612 is implemented using the components of the example computer system 300 illustrated and described in more detail with reference to FIG. 3. Likewise, embodiments of the intra-operative database 612 can include different and/or additional components or can be connected in different ways.

The intra-operative database 612 can include operation data, which may include, but not be limited to, real-time imaging data, pre-plans for operation, types of operations, surgical sites, and expected outcomes of the surgical procedures, which is shown in FIG. 7. For example, the intra-operative database 612 includes data for "Alex," who is 34 years old and weighs 74 kilograms. Further, Alex is diagnosed with a leg fracture and has images—Image 1, Image 2, and Image 3 from his X-rays and MRIs. Further, the family history for Alex includes high blood pressure to Alex's mother, diabetes to Alex's father, and Alex's grandfather died of kidney cancer. In addition, the real-time imaging data for Alex includes an image of Alex's left leg, an MRI scan, and an image of Alex's right leg. Further, a pre-plan for operation on Alex includes medication for numbing the left leg. The type of operation is surgical operation for fracture. Further, the surgical site is lower portion of left leg, and the expected outcome is a stable left leg with no pain and no side-effects—including normal blood pressure. Further, the intra-operative database 612 may include information related to the personnel manifest 610e, as discussed above. In one exemplary embodiment, the intra-operative database 612 includes data for Maria who is a scrub technician in the operating room, who has an experience of 2 years and whose medical condition is normal. Further, the intra-operative database 612 includes data for Peter who is a nurse in the operating room, who has an experience of 1 year and whose medical condition is normal. Further, the intra-operative database 612 includes data for Troy who is a circulating technician in the operating room, who has an experience of 3 years and whose medical condition is normal.

FIG. 8 illustrates a structure of an example historical database 614 for real-time robotic surgical assistance in an operating room, in accordance with one or more embodiments. An example operating room 102 is illustrated and described in more detail with reference to FIG. 1. The historical database 614 may include historical data related to all patients in the OR, one or more intra-operative data, and post-operative data, as illustrated by FIG. 8. The historical database 614 is implemented using the components of the example computer system 300 illustrated and described in more detail with reference to FIG. 3. Likewise, embodiments of the historical database 614 can include different and/or additional components or can be connected in different ways.

In embodiments, the one or more intra-operative data may include all information that happened during the surgical procedure or operation such as, but not limited to, length of the operation, equipment used in the operation, and surgical workflow. In one exemplary embodiment, equipment used in the operation may include implants and tools. The post-operative data may include one or more data related to post-operative follow-up with surgeon and patient survey data. The one or more data related to post-operative follow-up with surgeon may include at least, but not limited to, MRI of the implant inserted during the operation, blood pressure of the patient, body temperature of the patient, and other data related to the patient. In embodiments, the patient survey data may include patient subjective outcomes, as shown by FIG. 8. In embodiments, the patient subjective outcomes may include patient reported outcome or data given by the patient themselves. In another embodiment, the patient subjective outcomes may include private phenomena only assessable by the patient. In one exemplary embodiment, the patient subjective outcomes include patient suffering from abdominal pain.

In embodiments, the historical database 614 includes data corresponding to different patients. For example, the data can include stored reference patient images and/or stored reference procedure data. The stored reference procedure data can describe previous surgical procedures associated with the different patients and the surgical procedure. For example, the stored reference procedure data can include, without limitation, one or more surgical plans (e.g., plans for similar prior patients), patient vitals from previous surgical procedures, adverse events or conditions, predicted adverse condition for previous procedures, robotic steps, images, data collected during previous surgical procedures, outcome data (e.g., efficacy of treatment, whether treatment goals met, etc.) Further, the historical database 614 can contain or retrieve all data associated with a particular diagnosis (like disc impingement or leg fracture). The historical database 614 can include information related to aspects of intra-operative data such as, but not limited to, length of operation, equipment used such as implants (like screws), tools (like drills), and surgical workflow followed. In embodiments, the historical database 614 may also include post-operative data such as, but not limited to, an MRI of the implant, blood pressure of the patient, temperature of the patient, and other data related to the patient. In another embodiment, the historical database 614 includes patient survey data such as patient subjective outcomes. Operations on the historical database 614 using the embodiments disclosed herein enables real-time robotic surgical assistance in an operating room by automatically recommending or predicting the surgical procedures.

Figure 9:
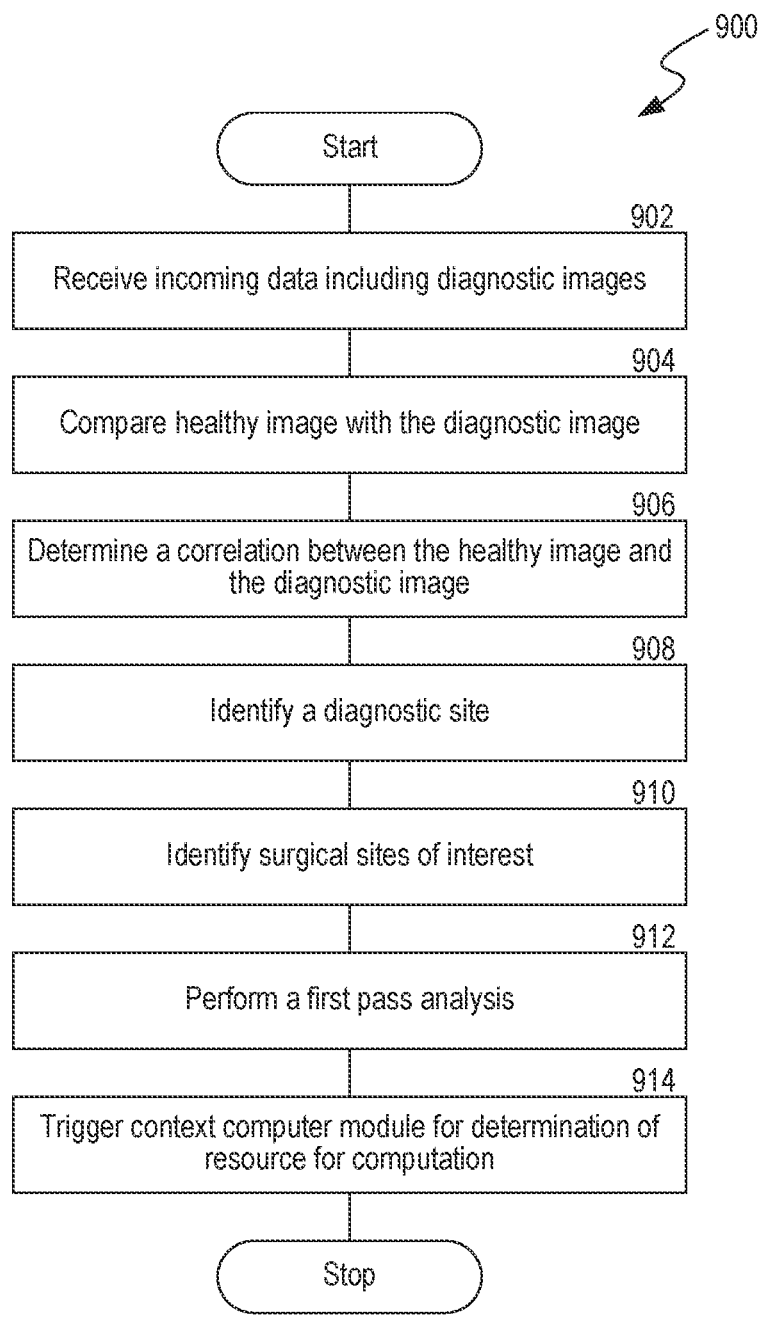
FIG. 9 is a flow diagram illustrating an example process for real-time robotic surgical assistance in an operating room, in accordance with one or more embodiments.

FIG. 9 is a flow diagram illustrating an example process 900 for real-time robotic surgical assistance in an operating room, in accordance with one or more embodiments. An example operating room 102 is illustrated and described in more detail with reference to FIG. 1. In some embodiments, the process 900 of FIG. 9 is performed by the imaging module 616. The imaging module 616 is illustrated and described in more detail with reference to FIG. 6. In other embodiments, the process 900 of FIG. 9 is performed by a computer system, e.g., the example computer system 300 illustrated and described in more detail with reference to FIG. 3. Particular entities, for example, the console 108 or the robotic surgical system 160 perform some or all of the steps of the process 900 in other embodiments. The console 108 and the robotic surgical system 160 are illustrated and described in more detail with reference to FIG. 1. Likewise, embodiments can include different and/or additional steps, or perform the steps in different orders.

The imaging module 616 can be configured to analyze one or more data received from the intra-operative database 612. In some alternative implementations, the steps shown by FIG. 9 can occur out of the order shown in FIG. 9. For example, two steps shown in succession in FIG. 9 can in fact be executed substantially concurrently or the steps may sometimes be executed in the reverse order, depending upon the functionality involved. In addition, the process descriptions in FIG. 9 can represent decisions made by a hardware structure such as a state machine.

In certain embodiments, the system 600 determines a physical condition of the patient by analyzing diagnostic images of the patient taken using one or more imaging devices. The analyzing includes correlating the diagnostic images to stored reference patient images. For example, the system 600 can perform digital image correlation and tracking, and image registration techniques for two-dimensional (2D) and three-dimensional (3D) measurements of differences between the diagnostic images and the stored reference patient images. In embodiments, a maximum of a correlation array between pixel intensity array subsets on two or more corresponding images is determined, which provides an integer translational shift between the diagnostic images and the stored reference patient images. The system 600 can further estimate shifts to a finer resolution than the resolution of the original diagnostic images and stored reference patient images, which is sometimes known as "subpixel" registration because the measured shift is smaller than an integer pixel unit. The system 600 identifies a diagnostic site from the diagnostic images based on the correlating. The diagnostic site is less correlated to a corresponding site in the stored reference patient images. The physical condition is associated with the diagnostic site. For example, in step 902, the imaging module 616 receives incoming data including diagnostic images. In embodiments, the diagnostic images may be received at least from the OR equipment 610, the sensors 610*a*, the anesthesia equipment 610*b*, the at least one surgical tool 610*c*, the at least one environment control equipment 610*d*, or the personnel manifest 610*e*. In an example embodiment, a diagnostic image may refer to an X-Ray of Alex's injured left leg.

In step 904, the imaging module 616 compares the diagnostic image with a stored reference patient image. In embodiments, the imaging module 616 compares the diagnostic image with the stored reference patient image to determine a medical problem of the patient. For example, the imaging module 616 compares the X-Ray of Alex's injured left leg with an X-Ray of a healthy left leg. The comparing can be performed using the correlation methods described herein.

In step 906, the imaging module 616 determines a correlation between the stored reference patient image and the diagnostic image using the correlation methods described herein. In embodiments, the correlation between the stored reference patient image and the diagnostic image indicates the condition of the diagnosed patient. For example, images of a bruised leg can have greater correlation to the stored reference patient image. In another example, images of a fractured leg can have less correlation to the stored reference patient image.

In step 908, based on the correlation between the stored reference patient image and the diagnostic image, the imaging module 616 identifies a diagnostic site. For example, the imaging module 616 identifies a region of the leg, which has undergone a fracture or disc impingement. The diagnostic site can be any body part of the patient, without departing from the scope of the disclosure. For example, the imaging module 616 identifies that Alex's left leg has a fracture at a lower end of the leg, near the ankle.

In some embodiments, a surgical procedure includes, without limitation, one or more of cutting tissue (incision), moving anatomical features, implanting a surgical implant, implanting a screw (screw location), and/or implanting a rod (rod location) performed by, e.g., a surgical robot. The system 600 identifies one or more surgical sites using a diagnostic site. Performing the surgical procedure, e.g., by the surgical robot, at the surgical site modifies the physical condition. For example, in step 910, based on the identification of the diagnostic site, the imaging module 616 identifies surgical sites of interest. Further, the surgical sites of interest can be identified based on a degree of injury to the patient. In another embodiment, the surgical sites of interest may be identified for location of cutting tissue (incision), screw location, and rod location. For example, the imaging module 616 identifies two surgical sites of interest on Alex's left leg for insertion of screws to cure Alex's fracture. In embodiments, based on the identification of the diagnostic site, the identification of the diagnostic site may identify one or multiple surgical sites of interest.

In some embodiments, analyzing diagnostic images includes determining a relative angle between vertebrae of the patient, determining that the relative angle is greater than a threshold angle, determining that the vertebrae are out of alignment, or identifying disc impingement of the patient. For example, in step 912, the imaging module 616 performs a first pass analysis. For example, performing the first pass analysis can include analyzing vertebrae, a relative angle between vertebrae, flag angles out of threshold data, vertebrae out of alignment, or disc impingement of the patient. In embodiments, the imaging module 616 performs the analysis without using the quantum computer 604. In embodiments, the first pass analysis may include using the classical computer 606 to analyze images received by the imaging module 616.

In step 914, the imaging module 616 triggers the context computer module 618 for determining a type of resource for computation. In embodiments, the type of resource may correspond to either a classical computer, a supercomputer, or a quantum computer. For example, the imaging module 616 analyzes the left leg of Alex to check that the leg is out of alignment due the fracture.

Figure 10:
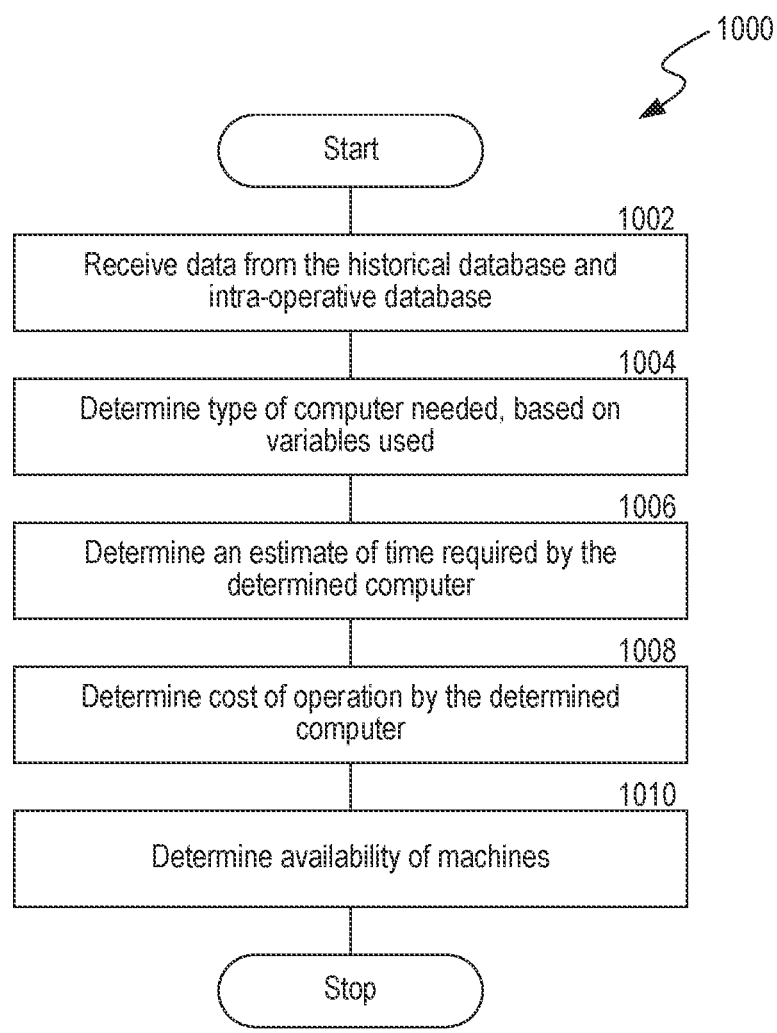
FIG. 10 is a flow diagram illustrating an example process for real-time robotic surgical assistance in an operating room, in accordance with one or more embodiments.

FIG. 10 is a flow diagram illustrating an example process 1000 for real-time robotic surgical assistance in an operating room, in accordance with one or more embodiments. An example operating room 102 is illustrated and described in more detail with reference to FIG. 1. In some embodiments, the process 1000 of FIG. 10 is performed by the context computer module 618. The context computer module 618 is illustrated and described in more detail with reference to FIG. 6. In other embodiments, the process 1000 of FIG. 10 is performed by a computer system, e.g., the example computer system 300 illustrated and described in more detail with reference to FIG. 3. Particular entities, for example, the console 108 or the robotic surgical system 160 perform some or all of the steps of the process 1000 in other embodiments. The console 108 and the robotic surgical system 160 are illustrated and described in more detail with reference to FIG. 1. Likewise, embodiments can include different and/or additional steps, or perform the steps in different orders.

The context computer module 618 can be configured to analyze one or more data received from the intra-operative database 612. In some alternative implementations, the steps of the process 1000 occur out of the order noted in the Drawings. For example, two steps shown in succession in conjunction with FIG. 10 may in fact be executed substantially concurrently or the blocks may sometimes be executed in the reverse order, depending upon the functionality involved. In addition, the process descriptions or steps in FIG. 1000 can represent decisions made by a hardware structure such as a state machine.

The context computer module 618 may determine that the quantum computer 604 is needed for providing real-time surgical assistance based on a number of variables that indicate a complexity of the surgical procedure and a computation time of the quantum computer 604 for providing the real-time surgical assistance. The complexity can vary with a number of images to be analyzed, an image resolution of the different images, complexity of input for the surgical robot, the time specified for the surgical robot or surgeon to receive the assistance, the number of computations for robotic movements of the surgical robot, etc. The context computer module 618 can include a complexity database with complexity data for surgical steps, computational resources, computer data, etc. For example, the quantum computer is identified for real-time surgical assistance when a complexity score for the procedures exceeds a threshold. The complexity score can be calculated based on the computational resources (e.g., computing power, processing clock speeds, etc.) needed to, for example, process image data without any or excess delays in surgical steps capable of being performed by a surgical robot, generate new instructions for the surgical robot, etc. For example, if the surgical robot can perform an incising step or implantation step within a time period (e.g., 1 minute, 5 minutes, 10 minutes, etc.), the complexity score can correspond to the computing resources (e.g., memory, processor resources, processor clock speeds, network speeds, etc.), needed to complete those steps within the time period. The time period can be included in a surgical plan input by a user, etc (see FIG. 4A and FIG. 5). The system 600 can determine and store resource values for available computing resources. The system 600 simulates procedures to predict complexity scores for the procedure. If the predicted complexity score exceeds a threshold, the system 600 determines whether a non-quantum computer, a quantum computer, or another computer is capable of meeting the predicted complexity score. If the quantum computer meets the complexity score requirements and the non-quantum computer does not, the system 600 selects the quantum computer for real-time surgical assistance. In embodiments, a particular computer for providing the surgical assistance is identified based on a processing speed of the particular computer, simulations, etc. In embodiments, the network capability of the particular computer is analyzed for data transfer between the particular computer and the surgical robot or the surgeon (see, e.g., the network adapter 312 and network 314 illustrated and described in more detail with reference to FIG. 3). The steps to be performed by the identified computer can be determined based on the resources of the computer. For example, in step 1002, the context computer module 618 receives data from the historical database 614 and the intra-operative database 612. Further, the context computer module 618 may receive information related to variables to be used for computing to be performed by the context computer module 618. In embodiments, the context computer module 618 may receive data from the intra-operative database 612 and the historical database 614.

In step 1004, the context computer module 618 determines a type of computer needed, based on the variables used. For example, the context computer module 618 may determine that the classical computer 606 should be used if 2-3 variables are required for computing. In another example, the context computer module 618 may determine that the supercomputer 608 should be used if 4-5 variables are required to be computed. In another example, the context computer module 618 may determine that the quantum computer 604 should be used if more than 10 variables are required to be computed. In embodiments, the determination of type of computer needed may be based on cost or safety or capability of the system 600. In embodiments, the determination of type of computer may be based on the aspect that the determination that the type of computer is performed within the timespan of surgical procedure.

In step 1006, the context computer module 618 determines an estimate of time required by the determined computer for the computation. In embodiments, the determination of estimate of time required may be a function of amount of data, number of variables, computational resources, and a desired confidence interval. In embodiments, the context computer module 618 may weigh data points and the number of variables to determine an effect on computation timeline of the system 600. For example, for an amount of data of 1 Gigabyte (GB) for five variables, the estimated time is 0.5 minutes. For usage in the OR, the time required by the determined computer may be minimum, to attain almost rea-time application during a surgical procedure.

In step 1008, the context computer module 618 determines the cost of operation by the selected computer. In embodiments, the cost of operation may act as a negative modifier for the selection of the type of resource. If the cost of operation is high, then system 600 might cut other options available, such that a particular cost is maintained. For example, use of the quantum computer increases the cost of operation based on the usage of complex variables involved. Further, the cost of operation may be determined as a matrix and may be a function of a score associated with the variables. It can be noted that the matrix may facilitate determining an appropriate cost for a particular computation. For example, for a surgical procedure for operating on Alex's left leg, the estimated cost with all the equipment and quantum computer is $500.

In step 1010, the context computer module 618 determines availability of machines. Based on the determination of estimated time and cost, the context computer module 618 determines availability of resources in the system 600. The availability of resources may be considered with the goal of attaining near real-time application of the resources in the OR.

FIG. 11 illustrates a structure of an example context computer database 620 for real-time robotic surgical assistance in an operating room, in accordance with one or more embodiments. An example operating room 102 is illustrated and described in more detail with reference to FIG. 1. The context computer database 620 may be coupled with the context computer module 618 to store one or more data generated by the context computer module 618. The context computer database 620 is implemented using the components of the example computer system 300 illustrated and described in more detail with reference to FIG. 3. Likewise, embodiments of the context computer database 620 can include different and/or additional components or can be connected in different ways.

The context computer database 620 may include information on, but not limited to, cost of resources, computational capability, and availability of resources. Further, the context computer database 620 may include the information corresponding to each type of resource available. In some embodiments, a particular computer used for providing real-time surgical assistance is a quantum computer, a classical computer, or a supercomputer. For example, the context computer database 620 includes information corresponding to the classical computer 606, the supercomputer 608, or the quantum computer 604. For example, the context computer database 620 includes information related to the classical computer 606 as cost of resource—$100, computation capability—1 GHz, and availability of 10 resources. In another example, the context computer database 620 includes information related to the supercomputer 608 as cost of resource—$300, computation capability—3 GHz, and availability of 7 resources. In another example, the context computer database 620 includes information related to the quantum computer 104 as cost of resource—$500, computation capability—5 GHz, and availability of 3 resources.

Figure 12:
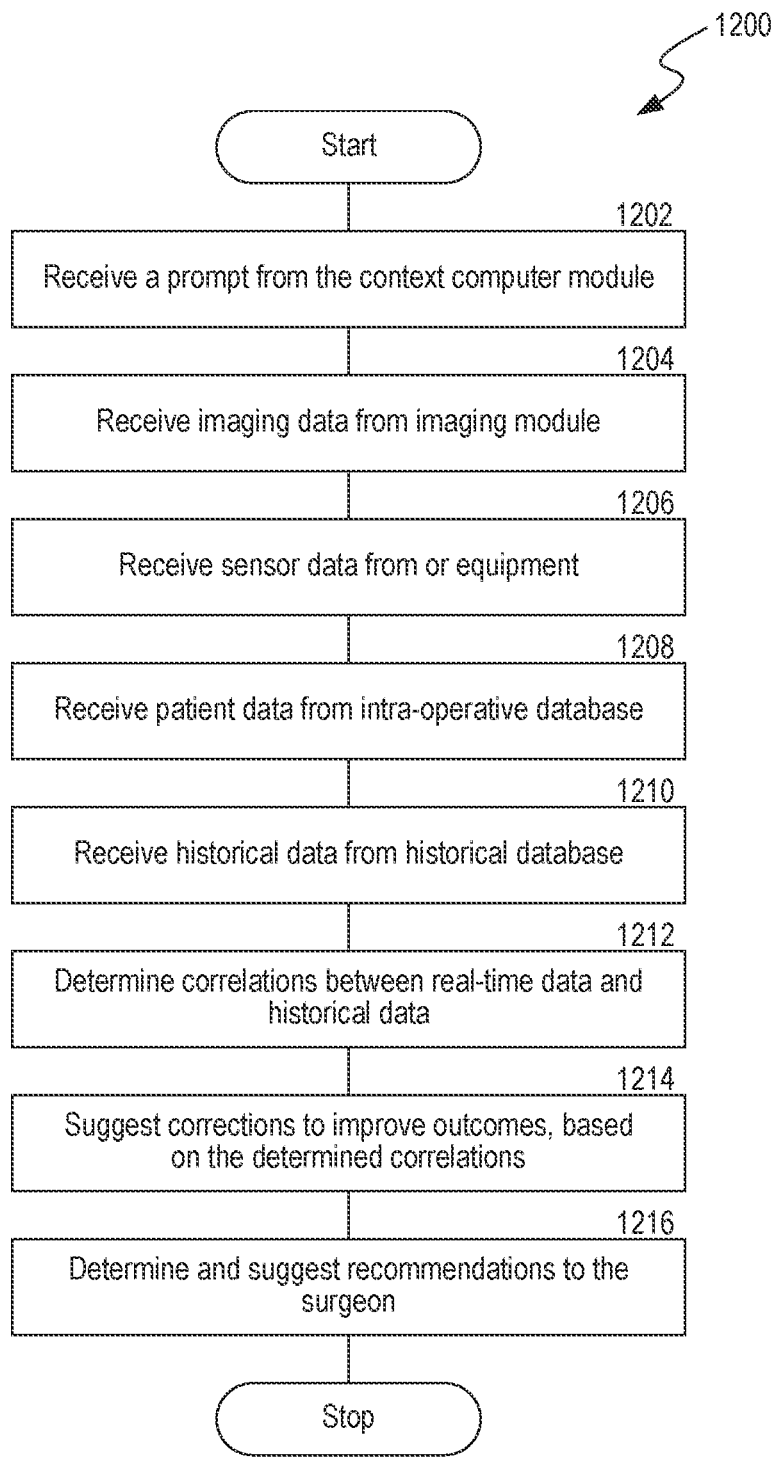
FIG. 12 is a flow diagram illustrating an example process for real-time robotic surgical assistance in an operating room, in accordance with one or more embodiments.

FIG. 12 is a flow diagram illustrating an example process 1200 for real-time robotic surgical assistance in an operating room, in accordance with one or more embodiments. An example operating room 102 is illustrated and described in more detail with reference to FIG. 1. In some embodiments, the process 1000 of FIG. 10 is performed by the quantum analysis module 622. The quantum analysis module 622 is illustrated and described in more detail with reference to FIG. 6. In other embodiments, the process 1200 of FIG. 12 is performed by a computer system, e.g., the example computer system 300 illustrated and described in more detail with reference to FIG. 3. Particular entities, for example, the console 108 or the robotic surgical system 160 perform some or all of the steps of the process 1200 in other embodiments. The console 108 and the robotic surgical system 160 are illustrated and described in more detail with reference to FIG. 1. Likewise, embodiments can include different and/or additional steps, or perform the steps in different orders.

In some alternative implementations, the steps in process 1200 may occur out of the order noted in the Drawings. For example, two steps shown in succession in FIG. 12 may in fact be executed substantially concurrently or the steps may sometimes be executed in the reverse order, depending upon the functionality involved. In addition, the process descriptions or steps can represent decisions made by a hardware structure such as a state machine.

In step 1202, the quantum analysis module 622 receives a prompt from the context computer module 618. In embodiments, the quantum analysis module 622 may perform real-time analysis for the surgical procedure. In some embodiments, real-time images of one or more surgical sites in a body of the patient undergoing the surgical procedure are captured. For example, the real-time images can include high-resolution video, X-rays, etc. The capturing is performed using one or more imaging devices. For example, in step 1204, the quantum analysis module 622 receives imaging data from the imaging module 616. In embodiments, the quantum analysis module 622 may receive the imaging data via the cloud network 602. Further, the quantum analysis module 622 may receive imaging data corresponding to the surgical procedure. For example, the quantum analysis module 622 receives X-rays corresponding to Alex's left leg depicting that the lower area of the left leg is fractured and needs surgery.

In some embodiments, the system 600 generates real-time sensor data using the one or more sensors 610*a* in the operating room. The real-time sensor data indicates one or more physiological parameters of the patient undergoing the surgical procedure. For example, in step 1206, the quantum analysis module 622 receives sensor data from the OR equipment 610. In embodiments, the quantum analysis module 622 may receive the sensor data via the cloud network 602. Further, the quantum analysis module 622 receives sensor data related to blood pressure of the patient. For example, the quantum analysis module 622 receives sensor data indicating that the blood pressure of Alex is 120/80 mmHg.

In some embodiments, the system 600 determines a physical condition of the patient by analyzing diagnostic images of the patient taken using one or more imaging devices. The analyzing includes correlating the diagnostic images to stored reference patient images. The system 600 identifies a diagnostic site from the diagnostic images based on the correlating. The diagnostic site is less correlated to a corresponding site in the stored reference patient images. The physical condition is associated with the diagnostic site. For example, in step 1208, the quantum analysis module 622 receives patient related data from the intra-operative database 112. In embodiments, the patient related data may include name, age, weight, diagnosis, patient images, and medical history of the patient and their family. For example, patient related data for Alex includes the name Alex, age 34, weight 74 kilograms, and images of Alex's left leg.

In step 1210, the quantum analysis module 622 receives historical data from the historical database 614. In embodiments, the historical data may correspond to a length of the operation, equipment used in the operation, and surgical workflow. For example, the historical data corresponding to Alex may represent that a previous surgery of duration of 4 hours was performed on the right leg of Alex.

In embodiments, the quantum analysis module 622 determines a prediction that the patient will experience an adverse condition during the surgical procedure based on the real-time images and the real-time sensor data. The determining can be performed using a machine learning module (see FIG. 2) trained using stored reference patient images, stored reference procedure data describing previous surgical procedures associated with the patient and the surgical procedure, etc. The stored reference procedure data can include patient vitals, outcomes, adverse conditions, or other patient related data. For example, the feature extraction module 208 can extract a feature vector of features from the real-time images and the real-time sensor data. The features can be indicative of bone positions, implant positions, surgical tool positions, etc. The machine learning module 200 determines the prediction based on the features. The machine learning module 200 can include the machine learning model 216 trained using features extracted from the stored reference patient images and stored reference procedure data describing previous surgical procedures associated with the patient and the surgical procedure. Training of the machine learning model 216 and operation of the machine learning module 200 is illustrated and described in more detail with reference to FIG. 2. In step 1212, the quantum analysis module 622 determines correlations between real-time data and historical data. In some embodiments, the adverse condition includes a blood pressure of the patient being greater than a threshold blood pressure, e.g., 135/90. Adjusting performing a surgical procedure, e.g., by the surgical robot, reduces the blood pressure. For example, a correlation between the real-time data and the historical data may indicate that Alex might have increased blood pressure during a surgery. Further, the historical data may indicate that a particular percentage of patients may experience increased pain post operation. For example, 15% of patients experience increased pain after an operation.

In some embodiments, the adverse condition includes a heart rate of the patient being greater than a threshold heart rate. The surgical procedure can be adjusted for avoiding or eliminating a detected or the predicted adverse condition. For example, new surgical modification instructions for a robotic surgery system can be generated to reduce the likelihood of the predicted adverse condition. A machine learning module trained using stored reference patient images and stored reference procedure data describing previous surgical procedures and prior patient conditions (e.g., adverse conditions) can be utilized. The systems disclosed herein can monitor patient vitals (e.g., blood pressure, heart rate, respiration rate, body temperature, ECG, arterial blood oxygen saturation, end-tidal carbon dioxide, etc.) and determine or predict whether the patient's vital exceed or will likely exceed a threshold value indicating an adverse condition.

In some embodiments, the quantum analysis module 622 generates surgical modification instructions for a surgical robot using the quantum computer. The surgical modification instructions are generated based on a prediction of an adverse patient condition by correlating real-time images of the surgical site and real-time sensor data to stored reference patient images and stored medical data (corresponding to previous surgical procedures) to provide real-time surgical assistance. For example, in step 1214, the quantum analysis module 622 generates corrections to improve outcomes, based on the determined correlations. In one example, a surgical robot may try to lower the blood pressure of the patient during the surgery so that the readings are in a normal or acceptable range before continuing with the operation. A surgical robot may allow another robot or an anesthesiologist to make corrections, based on the determined correlations. For example, for Alex, a surgical robot makes corrections to decrease Alex's blood pressure by 10 mmHg.

In some embodiments, a surgeon or a surgical robot adjusts performing a surgical procedure based on surgical modification instructions. The adjusting can include modifying movement of one or more surgical tools 154 at one or more surgical sites or modifying a medication administered to the patient. For example, in step 1216, the quantum analysis module 622 generates and sends recommendations to a surgical robot. The quantum analysis module 622 can determine how the patient reacts to a screw in a particular anatomical location. In an example, 85% of patients react to the screw in a particular anatomical location poorly. Thus, the quantum analysis module 622 instructs the surgical robot to modify the screw placement, for example, 1 cm above the planned site on Alex's left leg. The suggestion may decrease chances of post-operative pain or poor outcomes. Further, the quantum analysis module 622 may suggest that the surgical robot wait until the blood pressure or oxygen saturation are in a normal range before proceeding with the operation. In embodiments, the quantum analysis module 622 may indicate that an increased OR time may result in lower risk from increased blood pressure or oxygen saturation.

In embodiments, the quantum analysis module 622 may search for the best possible outcomes for the patient, such as surviving a critical operation, minimizing recovery time of the patient, minimizing post-operative pain of the patient, or minimizing deficits post operation. Further, the deficits may correspond to motor deficits, e.g., range of motion limitations. Also, the deficits may correspond to neural deficits like numbness, tingling, or paralysis post operation. The deficits may correspond to cardiovascular deficits such as cardiac impairment or heart failure. For example, Alex's blood pressure is optimized based on the recommendations of the quantum analysis module 622.

Figure 13:
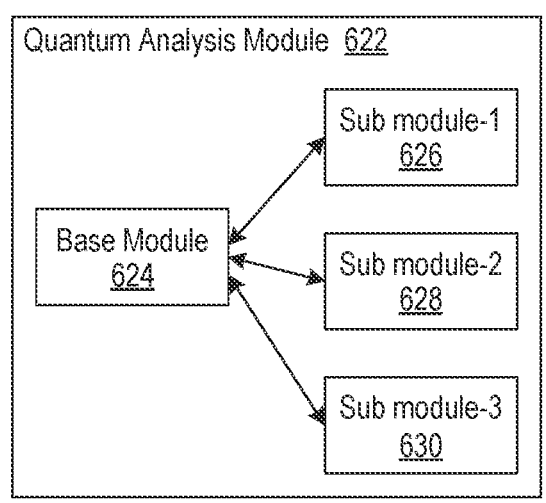
FIG. 13 illustrates a structure of an example quantum analysis module for real-time robotic surgical assistance in an operating room, in accordance with one or more embodiments.

FIG. 13 illustrates a structure of an example quantum analysis module 622 for real-time robotic surgical assistance in an operating room, in accordance with one or more embodiments. An example operating room 102 is illustrated and described in more detail with reference to FIG. 1. In embodiments, the system 600 includes the quantum analysis module 622, configured to collect and perform quantum analysis of real-time data and historical data in order to provide recommendations to a surgical robot by continuously monitoring the present status of the patient. The quantum analysis module 622 is implemented using the components of the example computer system 300 illustrated and described in more detail with reference to FIG. 3. Likewise, embodiments of the quantum analysis module 622 can include different and/or additional components or can be connected in different ways.

In some embodiments, a particular computer used for providing real-time surgical assistance is a quantum computer, a classical computer, or a supercomputer. For example, the quantum analysis module 622 can run on the quantum computer 604, using information from the historical database 614. The quantum analysis module 622 may have the ability to find patterns in information that the classical computers might struggle with. Further, the quantum analysis module 622 may utilize quantum computing for digital data processing based on the fundamental principles by which nature operates, i.e., quantum mechanics. Quantum mechanics is related to the use of a regular transistor present in many modern computers or devices. A transistor operates by directing large clouds of carriers of electrical current using engineered materials and quantum-based principles (band structure, localized states, etc.), thus producing behavior unusual for naturally found materials—an ability to precisely control current with current, or current via light, or light via current. In embodiments, the quantum computer 604 and associated quantum computing may enable a range of disruptive use cases for providers and health plans by accelerating diagnoses, personalizing medicine, and optimizing pricing. For example, the quantum computer 604 may be used to direct a radiation beam that destroys the cancer cells with extreme precision and spares all surrounding tissue.

The context computer module 618 may have determined that the quantum computer 604 is needed for providing real-time surgical assistance based on a number of variables that indicate a complexity of the surgical procedure and a computation time of the quantum computer 604 for providing the real-time surgical assistance. For example, the quantum analysis module 622 applied to the quantum computer 604 may find patterns in data received from databases, which have a large number of variables. In example embodiments, the number of variables may be more than 50. The complexity can vary with a number of images to be analyzed, an image resolution of the different images, the types of image processing techniques to be used (e.g., image segmentation, feature identification, renderings, etc.), the time specified for the surgical robot or surgeon to receive the assistance, the number of computations for robotic movements of the surgical robot, etc. The particular computer for providing the surgical assistance is identified based on a processing speed of the particular computer, simulations, etc. In embodiments, the network capability is analyzed for data transfer between the particular computer and the surgical robot or the surgeon as described herein. The quantum analysis module 622 may be able to perform correlations on the received data. Further, the correlations performed may be at least one of a linear correlation, a parabolic correlation, and a logarithmic regression correlation. For example, the quantum analysis module 612 may perform ordinary least square (OLS) for estimating the unknown parameters in a linear regression model. In another embodiment, the quantum analysis module 122 may perform convolution on the variables to find patterns in information received from the database. The quantum analysis module 622 may use any type of correlation, without departing from the scope of the disclosure, to find patterns in information received from the historical database 614.

In embodiments, the quantum analysis module 622 determines a prediction that the patient will experience an adverse condition based on the real-time images and the real-time sensor data. The determining can be performed using a machine learning module (see FIG. 2) trained using stored reference patient images and stored reference procedure data describing previous surgical procedures associated with the patient and the surgical procedure. For example, the quantum analysis module 622 is implemented to predict a future state of the patient or any associated health condition. In some embodiments, the adverse condition includes a blood pressure of the patient being greater than a threshold blood pressure, e.g., 135/90. Adjusting performing a surgical procedure, e.g., by the surgical robot, reduces the blood pressure. For example, the future state of the patient can refer to a future blood pressure of the patient, such as two days after the operation. Such prediction facilitates prescription of a proactive medicine for the patient to administer safe medication based on the prediction. For example, if the quantum analysis module 622 predicts that the blood pressure for Alex is going to rise 10 mmHg above his normal blood pressure after undergoing a leg surgery, Alex's surgeon can provide a proactive medication to reduce the blood pressure. In another example, if the patient is predicted to lose stability, a surgical robot may pause the surgical procedure or prefer a different procedure. In another example, if during leg surgery of Alex the quantum analysis module 622 predicts that the blood pressure for Alex is going to rise abruptly which could put Alex in danger of a heart attack, then the surgical robot could pause the surgery or may use medication to lower the risk of increasing blood pressure of Alex, thus preventing the loss of stability of Alex's medical condition. Further, the quantum analysis module 622 may determine tolerance of a patient. For example, a patient with low tolerance may indicate that the surgical robot has to perform a surgery slowly or even break up a major surgery into several surgeries.

In embodiments, the quantum analysis module 622 may include a base module 624, a sub module-1 626, a sub module-2 628, and a sub module-3 630. The base module 624 may collect data and be used to run the sub module-1 626, sub module-2 628, and sub module-3 630. Such use of the quantum computer 604 may facilitate timely analysis or prediction during a surgical procedure in the OR. Further, on comparison, the classical computer 606 can take days or years to perform similar analysis or predictions. Further, such use of the quantum computer 604 or the quantum analysis module 622 facilitates real-time analysis of complex medical data.

Figure 14:
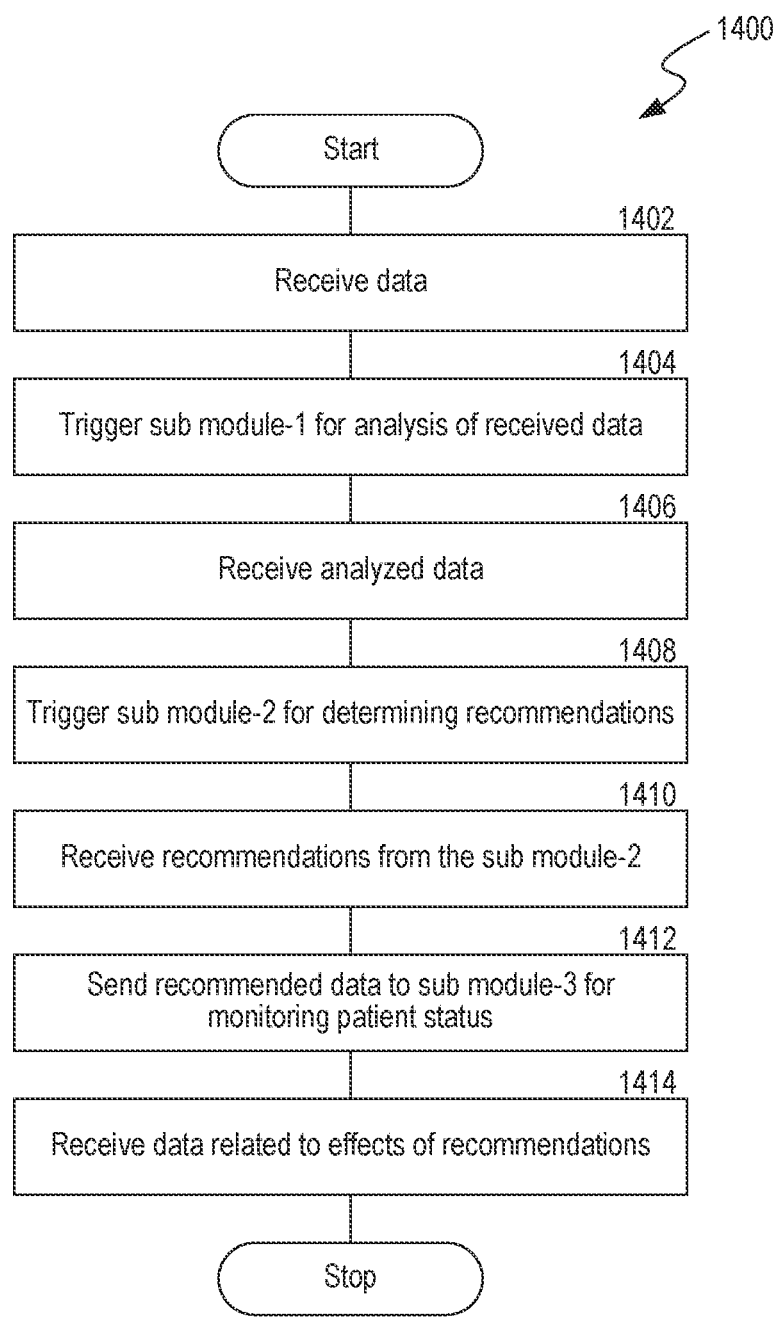
FIG. 14 is a flow diagram illustrating an example process for real-time robotic surgical assistance in an operating room, in accordance with one or more embodiments.

FIG. 14 is a flow diagram illustrating an example process 1400 for real-time robotic surgical assistance in an operating room, in accordance with one or more embodiments. An example operating room 102 is illustrated and described in more detail with reference to FIG. 1. In some embodiments, the process 1400 of FIG. 14 is performed by the base module 624. The base module 624 is illustrated and described in more detail with reference to FIG. 6. In other embodiments, the process 1400 of FIG. 14 is performed by a computer system, e.g., the example computer system 300 illustrated and described in more detail with reference to FIG. 3. Particular entities, for example, the console 108 or the robotic surgical system 160 perform some or all of the steps of the process 1400 in other embodiments. The console 108 and the robotic surgical system 160 are illustrated and described in more detail with reference to FIG. 1. Likewise, embodiments can include different and/or additional steps, or perform the steps in different orders.

In some alternative implementations, the functions indicated by the steps of process 1400 may occur out of the order noted in the Drawings. For example, two steps shown in succession in FIG. 14 may in fact be executed substantially concurrently or the steps may sometimes be executed in the reverse order, depending upon the functionality involved. In addition, the process descriptions or steps in flow charts can represent decisions made by a hardware structure such as a state machine.

In some embodiments, the base module 624 performs a computer-implemented method for providing real-time surgical assistance to a surgical robot. For example, in step 1402, the base module 624 receives data from the OR equipment 610, the intra-operative database 612, or the historical database 614. Further, the data received from the intra-operative database 612 and the historical database 614 may include patient related data such as name, age, weight, diagnosis, or family medical history. The data received from the intra-operative database 612 and the historical database 614 may include intra-operative data such as a length of the operation, equipment used, or post-operative data such as follow-ups with the surgeon or patient survey data. Further, the base module 624 may receive real-time data related to patient and the associated surgical procedure. For example, Alex is undergoing a surgical procedure for a fracture in his left leg. Historical data related to a surgical procedure regarding a fracture of a left leg that indicates that the blood pressure of the patient usually increases during the operation or while inserting screws in the leg is received.

In step 1404, the base module 624 triggers the sub module-1 626 for analysis of received data. Based on the received data, the sub module-1 626 may be used to find patterns or similar data which might resemble the received real-time data. The use of the sub module-1 626 is explained in conjunction with FIG. 15.

In step 1406, the base module 624 receives the analyzed data from the sub module-1 626. Such analysis of the sub module-1 626 may assist a surgical robot in using information from previous surgical procedures to improve performance of a current surgical procedure. For example, based on the historical data, a surgical robot can avoid the condition of increased blood pressure for Alex by taking proper measures beforehand, such as indicating a particular drug to stabilize Alex's blood pressure.

In step 1408, the base module 624 triggers the sub module-2 628. The use of the sub module-2 628 is explained in conjunction with FIG. 16. In embodiments, the sub module-2 628 is referred to as a recommendation module. The sub module-2 628 may provide recommendations to a surgical robot during an ongoing surgical procedure on the patient.

In embodiments, a surgical procedure includes cutting tissue (incision), implanting a screw (screw location), or implanting a rod (rod location) performed by, e.g., a surgical robot. The system 600 identifies one or more surgical sites using a diagnostic site. Performing the surgical procedure, e.g., by the surgical robot, at the surgical site modifies the physical condition. For example, in step 1410, the base module 624 receives recommendations from the sub module-2 628. In some embodiments, adjusting a surgical procedure includes modifying placement of a screw at a surgical site. For example, during the surgical procedure for Alex, while implanting a screw in Alex's left leg, the sub module-2 628 generates an advanced solution of shifting the location of the screw by 1 cm. Further, a surgical robot may request an additional recommendation from the system 600. In embodiments, the sub module-2 628 may provide specific modifications for the surgical procedure.

In step 1412, the base module 624 sends recommended data to the sub module-3 630 for monitoring patient status. The use of the sub module-3 630 is explained in conjunction with FIG. 17. The sub module-3 630 may be used for monitoring real time data related to blood pressure, SpO2, heartbeat, etc., of the patient.

In step 1414, the base module 624 receives data related to effects of recommendations on the patient from the sub module-3 630. For example, the base module 624 receives information that the blood pressure of Alex has increased by 10 mmHg.

Figure 15:
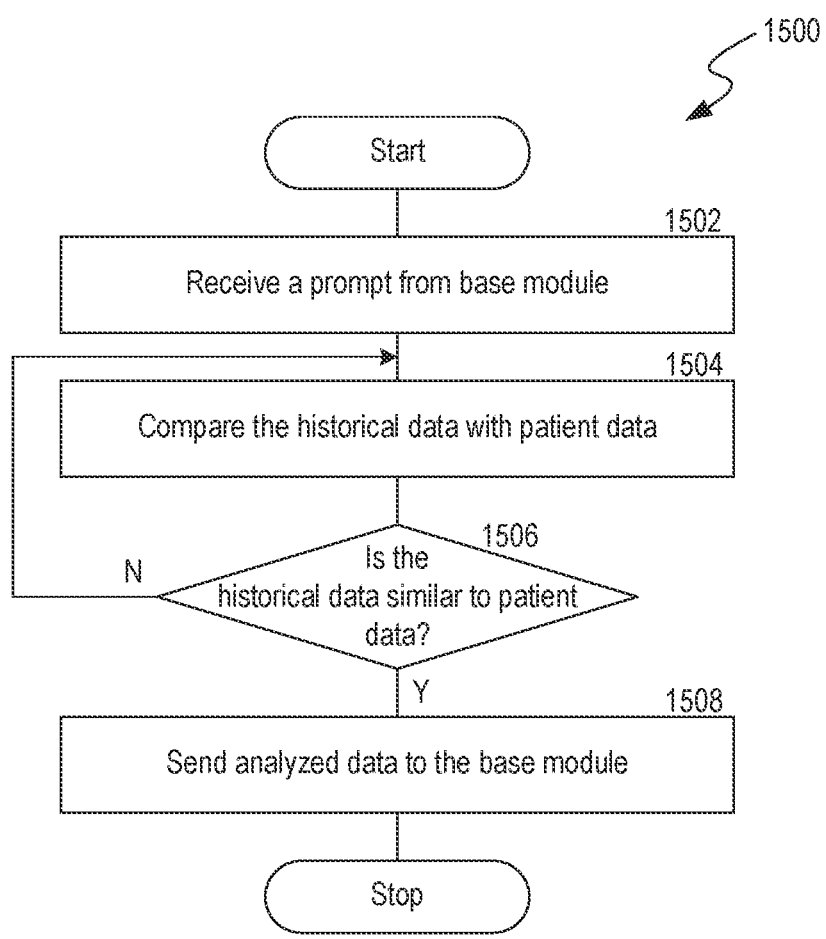
FIG. 15 is a flow diagram illustrating an example process for real-time robotic surgical assistance in an operating room, in accordance with one or more embodiments.

FIG. 15 is a flow diagram illustrating an example process 1500 for real-time robotic surgical assistance in an operating room, in accordance with one or more embodiments. An example operating room 102 is illustrated and described in more detail with reference to FIG. 1. In some embodiments, the process 1500 of FIG. 15 is performed by the sub module-1 626. The sub module-1 626 is illustrated and described in more detail with reference to FIG. 13. In other embodiments, the process 1500 of FIG. 15 is performed by a computer system, e.g., the example computer system 300 illustrated and described in more detail with reference to FIG. 3. Particular entities, for example, the console 108 or the robotic surgical system 160 perform some or all of the steps of the process 1500 in other embodiments. The console 108 and the robotic surgical system 160 are illustrated and described in more detail with reference to FIG. 1. Likewise, embodiments can include different and/or additional steps, or perform the steps in different orders.

In some alternative implementations, the functions indicated by the steps of process 1500 may occur out of the order noted in the Drawings. For example, two steps shown in succession in FIG. 15 may in fact be executed substantially concurrently or the steps may sometimes be executed in the reverse order, depending upon the functionality involved. In addition, the process descriptions or step in flow charts can represent decisions made by a hardware structure such as a state machine.

In step 1502, the sub module-1 626 receives a prompt from the base module 624. The sub module-1 626 may be triggered to run analysis on the received data. In step 1504, the sub module-1 626 compares the historical data with the patient data. Based on the received data, the sub module-1 626 may find patterns or similar data which might resemble the received real-time data. Such analysis by the sub module-1 626 may assist a surgical robot in using information from previous surgical procedures to perform or improve a current surgical procedure. In step 1506, the sub module-1 626 determines if the historical data is similar to the patient data.

In step 1508, if the historical data is similar to the patient data, then the sub module-1 626 may send the analyzed data to the base module 624. For example, Alex is undergoing a surgical procedure for a fracture in his left leg. Historical data related to a surgical procedure regarding fracture of a left leg that indicates that the blood pressure of the patient usually increases during the operation or while inserting screws in the leg is analyzed. In some embodiments, a surgeon or a surgical robot adjusts performing a surgical procedure based on surgical modification instructions. The adjusting can include modifying movement of one or more surgical tools 154 at one or more surgical sites or modifying a medication administered to the patient. For example, based on the historical data of the increasing blood pressure of patients during the operation, a surgical robot can avoid the increased blood pressure condition for Alex by taking proper measures beforehand, such as recommending a particular drug to stabilize Alex's blood pressure. In another scenario, if the historical data is not similar to the patient data, then the sub module-1 626 may proceed to step 1504 to compare the historical data with the patient data.

Figure 16:
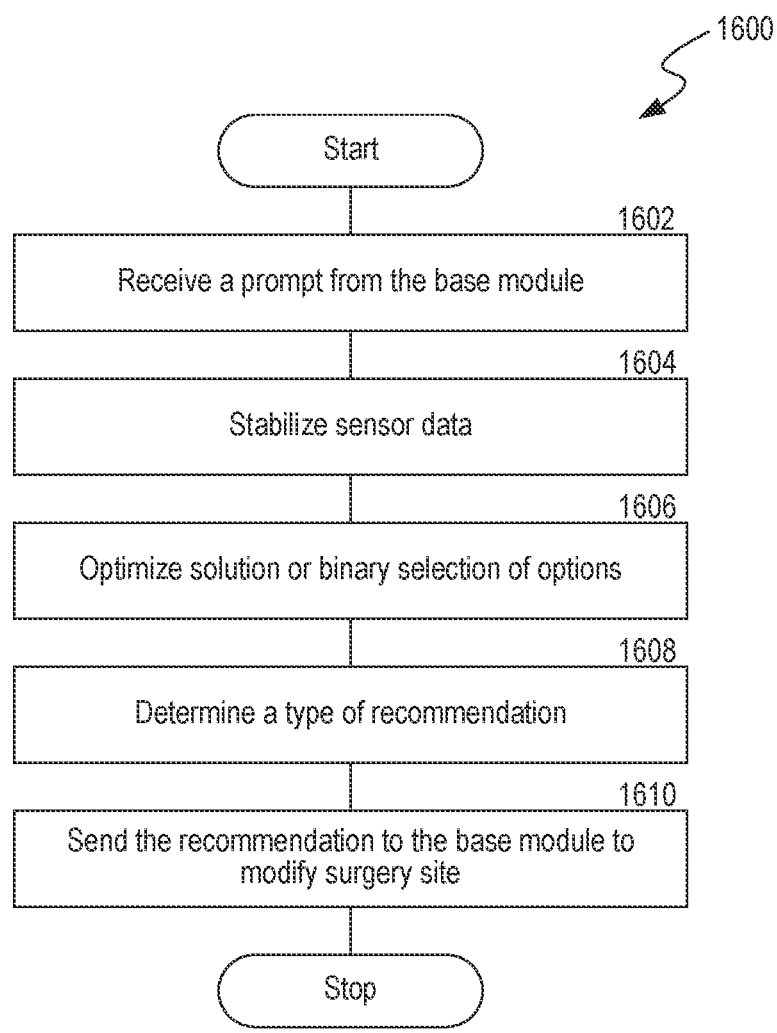
FIG. 16 is a flow diagram illustrating an example process for real-time robotic surgical assistance in an operating room, in accordance with one or more embodiments.

FIG. 16 is a flow diagram illustrating an example process 1600 for real-time robotic surgical assistance in an operating room, in accordance with one or more embodiments. An example operating room 102 is illustrated and described in more detail with reference to FIG. 1. In some embodiments, the process 1600 of FIG. 16 is performed by the sub module-2 628. The sub module-2 628 is illustrated and described in more detail with reference to FIG. 13. In other embodiments, the process 1600 of FIG. 16 is performed by a computer system, e.g., the example computer system 300 illustrated and described in more detail with reference to FIG. 3. Particular entities, for example the console 108 or the robotic surgical system 160, perform some or all of the steps of the process 1600 in other embodiments. The console 108 and the robotic surgical system 160 are illustrated and described in more detail with reference to FIG. 1. Likewise, embodiments can include different and/or additional steps or perform the steps in different orders.

In some alternative implementations, the functions indicated by the steps of process 1600 may occur out of the order noted in the Drawings. For example, two steps shown in succession in FIG. 16 may in fact be executed substantially concurrently or the steps may sometimes be executed in the reverse order, depending upon the functionality involved. In addition, the process descriptions or step in flow charts can represent decisions made by a hardware structure such as a state machine.

In step 1602, the sub module-2 628 receives a prompt from the base module 624. Further, the sub module-2 628 may receive analyzed data from the base module 624. In embodiments, the sub module-2 628 may be referred to as a recommendation module. The sub module-2 628 may provide recommendations to a surgical robot during an ongoing surgical procedure on the patient.

In step 1604, the sub module-2 628 stabilizes the sensor data. Stabilizing the sensor data may include 3D rotation-based stabilization of data. For example, the patient's blood pressure is increasing at a critical point in the surgery that correlates to poor patient outcomes when performed in patients with high blood pressure (as determined by the quantum computer, supercomputer, or classical computer). The sub module-2 628 may recommend that the procedure be delayed, and the blood pressure be addressed by administering medication, adjusting anesthesiology parameters, or some other treatment. When the blood pressure returns to a normal range, the sub module-2 628 may recommend that the surgical robot continue the surgical procedure.

In some embodiments, adjusting a surgical procedure includes modifying placement of a screw at a surgical site. For example, in step 1606, the sub module-2 628 optimizes a solution or provides a binary selection of options. For example, during the surgical procedure for Alex, while implanting a screw in Alex's left leg, the sub module-2 628 provides an optimized solution of shifting the location of the screw by 1 cm. Further, the sub module-2 628 may provide a binary selection of options for the surgical robot. For example, during the surgical procedure for Alex, while implanting a screw in Alex's left leg, the sub module-2 628 provides a recommendation such as a "yes" or a "no." In one scenario, if the location of implanting the screw is correct, then the sub module-2 628 indicates that it is correct. In another scenario, if the location of implanting the screw is incorrect, then the sub module-2 628 indicates that it is incorrect. The binary selection may be ambiguous and tedious for a surgeon and hence is performed by a surgical robot.

In one scenario, the sub module-2 628 provides optimized solutions if the data received from the sub module-1 626 can be computed in a timely manner. For example, during the surgical procedure for Alex, while implanting a screw in Alex's left leg, the sub module-2 628 provides an advanced solution of shifting the location of the screw by 1 cm. In another case, the sub module-2 628 provides a binary selection if the data received from the sub module-1 626 is too large. For example, a "yes" or a "no" response is received for a query by a surgical robot or a surgeon, e.g., "should we pause the surgery?" Further, the surgical robot may request an additional recommendation from the system 600.

In step 1608, the sub module-2 628 determines a type of recommendation. The recommendation may be to increase a particular type of medication for the patient or a change or modification in the surgical site of an implant or screw. For example, the sub module-2 628 determines that a medication shall be given to Alex to reduce the blood pressure by 10 mmHg. In some embodiments, the sub module-2 628 generates surgical modification instructions for a surgical robot using the quantum computer. The surgical modification instructions are generated based on a prediction of an adverse patient condition by correlating real-time images of the surgical site and real-time sensor data to stored reference patient images and stored medical data (corresponding to previous surgical procedures) to provide real-time surgical assistance. For example, the sub module-2 628 can provide specific modifications for the surgical procedure.

In step 1610, the sub module-2 628 sends the determined recommendations to the base module 624 to modify a surgical site. The base module 624 may use the determined recommendation to modify the surgical site. For example, during the surgical procedure for Alex, while implanting a screw in Alex's left leg, the base module 624 provides a recommendation for shifting the location of the screw by 1 cm.

Figure 17:
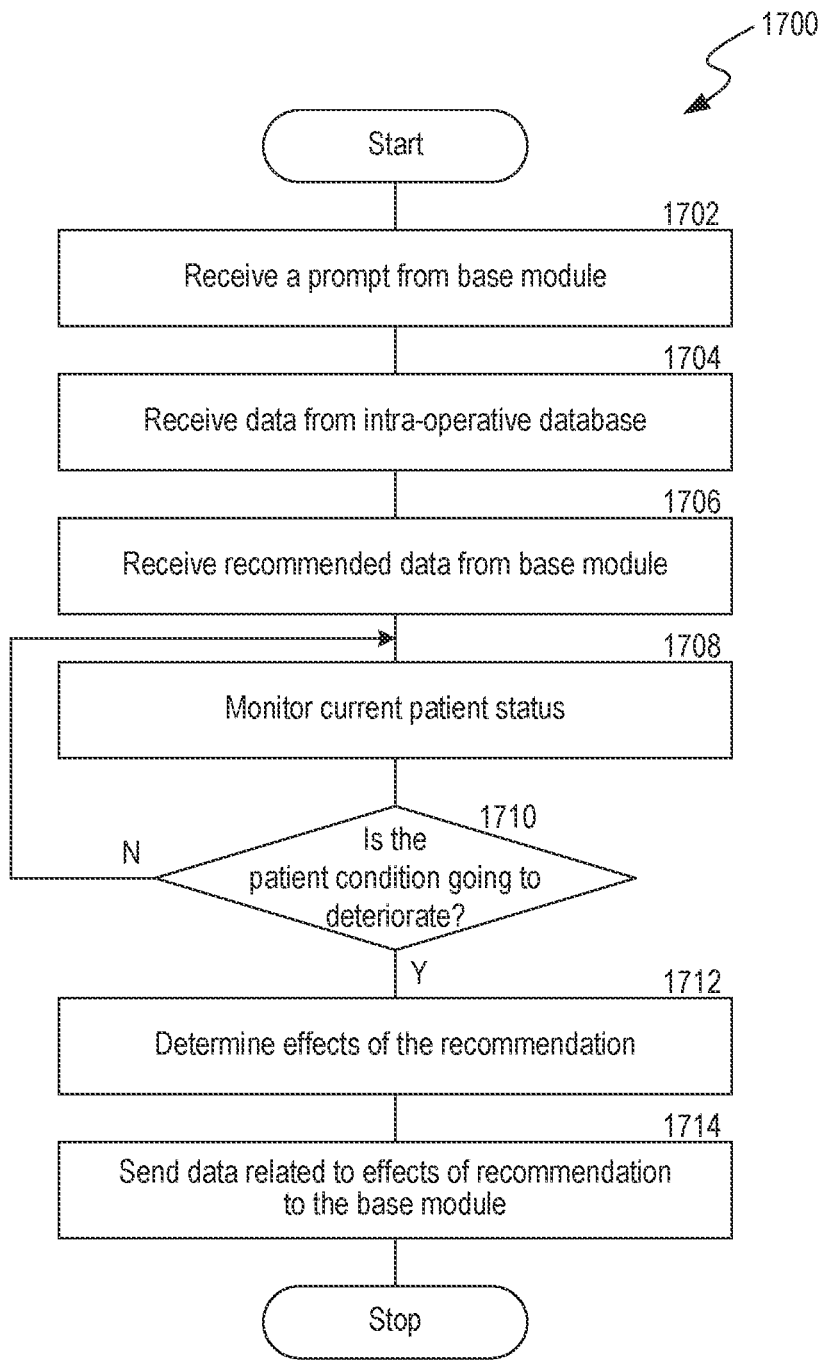
FIG. 17 is a flow diagram illustrating an example process for real-time robotic surgical assistance in an operating room, in accordance with one or more embodiments.

FIG. 17 is a flow diagram illustrating an example process 1700 for real-time robotic surgical assistance in an operating room, in accordance with one or more embodiments. An example operating room 102 is illustrated and described in more detail with reference to FIG. 1. In some embodiments, the process 1700 of FIG. 17 is performed by the sub module-3 630. The sub module-3 630 is illustrated and described in more detail with reference to FIG. 13. In other embodiments, the process 1700 of FIG. 17 is performed by a computer system, e.g., the example computer system 300 illustrated and described in more detail with reference to FIG. 3. Particular entities, for example the console 108 or the robotic surgical system 160, perform some or all of the steps of the process 1700 in other embodiments. The console 108 and the robotic surgical system 160 are illustrated and described in more detail with reference to FIG. 1. Likewise, embodiments can include different and/or additional steps or perform the steps in different orders.

In some alternative implementations, the functions indicated by the steps of process 1700 may occur out of the order noted in the Drawings. For example, two steps shown in succession in FIG. 17 may in fact be executed substantially concurrently or the steps may sometimes be executed in the reverse order, depending upon the functionality involved. In addition, the process descriptions or steps in flow charts can represent decisions made by a hardware structure such as a state machine.

In step 1702, the sub module-3 630 receives a prompt from the base module 624. The sub module-3 630 may monitor the patient status. In step 1704, the sub module-3 630 receives data from the intra-operative database 612. The sub module-3 630 facilitates real-time collection of hospital data. In step 1706, the sub module-3 630 receives recommended data from the base module 624. The sub module-3 630 may receive recommended data from the base module 624 for monitoring the patient status.

In step 1708, the sub module-3 630 monitors a current patient status. For example, the surgical robot has inserted the screw in Alex's left leg and Alex is having normal blood pressure of 120/80 mmHg. In step 1710, the sub module-3 630 determines if the patient condition is going to deteriorate. In one scenario, if the sub module-3 630 determines that the patient condition is not going to deteriorate, then the sub module-3 630 proceeds to step 1708 to monitor the current patient status. For example, Alex's blood pressure is normal during the surgical procedure. In another scenario, if the sub module-3 630 determines that the patient condition is going to deteriorate, then the sub module-3 630 may determine the effects of the recommendation in step 1712. For example, the sub module-3 630 determines that Alex's blood pressure is increasing.

In step 1714, the sub module-3 630 sends data related to the effects of the recommendation to the base module 624. For example, the sub module-3 630 sends the information related to the increasing blood pressure of Alex to the base module 624.

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example, using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A computer-implemented method for providing real-time surgical assistance to a surgical robot comprising:

determining that a particular computer is to provide for the real-time surgical assistance based on a number of variables indicating a complexity of a surgical procedure and a computation time of the particular computer for providing the real-time surgical assistance;

capturing, using one or more sensors, real-time sensor data indicating one or more physiological parameters of a patient undergoing the surgical procedure;

determining a prediction that the patient will experience an adverse condition during the surgical procedure, based on the real-time sensor data, using a machine learning module trained using stored reference patient data and stored reference procedure data describing previous surgical procedures associated with the surgical procedure;

generating surgical modification instructions for the surgical robot using the particular computer based on the prediction by correlating the real-time sensor data to the stored reference patient data and the stored reference procedure data to provide the real-time surgical assistance; and adjusting performing surgical procedure, by the surgical robot, based on the surgical modification instructions, the adjusting comprising modifying movement of a surgical tool to avoid the adverse condition.

2. The method of claim 1, wherein the stored reference patient data comprises stored reference patient images, the method comprising:

determining a physical condition of the patient by analyzing diagnostic images of the patient taken using an imaging device, the analyzing comprising correlating the diagnostic images to the stored reference patient images; and identifying a diagnostic site from the diagnostic images, the diagnostic site being less correlated to a corresponding site in the stored reference patient images, the physical condition associated with the diagnostic site.

3. The method of claim 2, wherein the surgical procedure comprises cutting tissue, implanting a screw, or implanting a rod, the method comprising:

identifying a surgical site using the diagnostic site, wherein performing the surgical procedure at the surgical site modifies the physical condition.

4. The method of claim 2, wherein analyzing the diagnostic images comprises:

scanning images of vertebrae of the patient.

5. The method of claim 1, wherein the adverse condition comprises a blood pressure of the patient being greater than a threshold blood pressure, and the adjusting reduces the blood pressure.

6. The method of claim 1, wherein the adjusting comprises modifying placement of a screw at the surgical site.

7. The computer-implemented method of claim 1, wherein the particular computer is a quantum computer.

8. A non-transitory computer-readable storage medium storing computer instructions for providing real-time surgical assistance to a surgical robot, the computer instructions when executed by one or more computer processors, cause the one or more computer processors to:

determine that a particular computer is to provide for real-time surgical assistance based on a number of variables indicating a complexity of a surgical procedure and a computation time of the particular computer for providing the real-time surgical assistance;

capture, using one or more sensors, real-time sensor data indicating one or more physiological parameters of a patient undergoing the surgical procedure;

determine a prediction that the patient will experience an adverse condition during the surgical procedure, based on the real-time sensor data, using a machine learning module trained using stored reference patient data and stored reference procedure data describing previous surgical procedures associated with the surgical procedure;

generate surgical modification instructions for the surgical robot using the particular computer based on the prediction by correlating the real-time sensor data to the stored reference patient data and the stored reference procedure data to provide the real-time surgical assistance; and adjust performing the surgical procedure, by the surgical robot, based on the surgical modification instructions, the adjusting comprising modifying movement of a surgical tool to avoid the adverse condition.

9. The non-transitory computer-readable storage medium of claim 8, wherein the stored reference patient data comprises stored reference patient images, and the computer instructions cause the one or more computer processors to:

determine a physical condition of the patient by analyzing diagnostic images of the patient taken using an imaging device, the analyzing comprising correlating the diagnostic images to the stored reference patient images; and identify a diagnostic site from the diagnostic images, the diagnostic site being less correlated to a corresponding site in the stored reference patient images, the physical condition associated with the diagnostic site.

10. The non-transitory computer-readable storage medium of claim 9, wherein the surgical procedure comprises cutting tissue, implanting a screw, or implanting a rod, and the computer instructions cause the one or more computer processors to:

identify a surgical site using the diagnostic site, wherein performing the surgical procedure at the surgical site modifies the physical condition.

11. The non-transitory computer-readable storage medium of claim 9, wherein the computer instructions to analyze the diagnostic images cause the one or more computer processors to scan images of vertebrae of the patient.

12. The non-transitory computer-readable storage medium of claim 8, wherein the adverse condition comprises a blood pressure of the patient being greater than a threshold blood pressure, and the adjusting reduces the blood pressure.

13. The non-transitory computer-readable storage medium of claim 8, wherein the adjusting comprises modifying placement of a screw at the surgical site.

14. The non-transitory computer-readable storage medium of claim 8, wherein the particular computer is a quantum computer.

15. A surgical system for providing real-time surgical assistance to a surgical robot, comprising:

one or more computer processors; and a non-transitory computer-readable storage medium storing computer instructions, which when executed by the one or more computer processors, cause the surgical system to:

determine that a particular computer is to provide for the real-time surgical assistance based on a number of variables indicating a complexity of a surgical procedure and a computation time of the particular computer for providing the real-time surgical assistance;

capture, using one or more sensors, real-time sensor data indicating one or more physiological parameters of a patient undergoing the surgical procedure;

determine a prediction that the patient will experience an adverse condition during the surgical procedure, based on the real-time sensor data, using a machine learning module trained using stored reference patient data and stored reference procedure data describing previous surgical procedures associated with the surgical procedure;

generate surgical modification instructions for the surgical robot using the particular computer based on the prediction by correlating the real-time sensor data to the stored reference patient data and the stored reference procedure data to provide the real-time surgical assistance; and adjust performing the surgical procedure, by the surgical robot, based on the surgical modification instructions, the adjusting comprising modifying movement of a surgical tool to avoid the adverse condition.

16. The surgical system of claim 15, wherein the stored reference patient data comprises stored reference patient images, and wherein the computer instructions cause the surgical system to:

determine a physical condition of the patient by analyzing diagnostic images of the patient taken using an imaging device, the analyzing comprising correlating the diagnostic images to the stored reference patient images; and identify a diagnostic site from the diagnostic images, the diagnostic site being less correlated to a corresponding site in the stored reference patient images, the physical condition associated with the diagnostic site.

17. The surgical system of claim 16, wherein the surgical procedure comprises cutting tissue, implanting a screw, or implanting a rod, and the computer instructions cause the surgical system to:

identify a surgical site using the diagnostic site, wherein performing the surgical procedure at the surgical site modifies the physical condition.

18. The surgical system of claim 16, wherein the computer instructions to identify the diagnostic images cause the surgical system to:

scan images of vertebrae of the patient.

19. The surgical system of claim 15, wherein the adverse condition comprises a blood pressure of the patient being greater than a threshold blood pressure, and the adjusting reduces reduce the blood pressure.

20. The surgical system of claim 15, wherein the computer instructions to adjust performing the surgical procedure cause the surgical system to modify placement of a screw at a surgical site.

* * * * *